(12) United States Patent
Tomlinson

(10) Patent No.: US 6,436,672 B1
(45) Date of Patent: Aug. 20, 2002

(54) POLYNUCLEOTIDES ENCODING A TYPE V ADENYLYL CYCLASE

(75) Inventor: James E. Tomlinson, Burlingame, CA (US)

(73) Assignee: Millennium Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 09/473,716

(22) Filed: Dec. 29, 1999

Related U.S. Application Data

(63) Continuation of application No. PCT/US98/13540, filed on Jul. 1, 1998, which is a continuation of application No. 08/886,362, filed on Jul. 1, 1997, now abandoned.
(60) Provisional application No. 60/070,901, filed on Jul. 1, 1997.

(51) Int. Cl.[7] .................................................. C12N 9/88
(52) U.S. Cl. .............. 435/69.1; 435/252.3; 435/254.11; 435/325; 435/419; 435/320.1; 536/23.1
(58) Field of Search ....................... 536/23.2; 435/320.1, 435/252.3, 325, 419, 254.11, 232

(56) References Cited

U.S. PATENT DOCUMENTS 6,107,076 A * 8/2000 Tang et al. ................. 435/232

FOREIGN PATENT DOCUMENTS

| EP | 529622 | 3/1993 |
|---|---|---|
| WO | WO95/30012 | 9/1995 |
| WO | PCT/US98/13540 | 11/1998 |

OTHER PUBLICATIONS

Wallach et al. Molecular cloning and expression of a novel type V adenylyl cyclase from rabbit myocardium. FEBS Letters (1994) 338:257–263.*

Defer et al., "Molecular cloning of the human type VIII adenylyl cyclase," FEBS Letters, 351:109–113, 1994.
Ishikawa et al., "Isolation and characterization of a novel cardiac adenylylcyclase cDNA," Jour. Biol. Chem., 267(19):13553–13557, 1992.
Nomura et al., "Prediction of the coding sequences of unidentified human genes. I. The coding sequences of 40 new genes (KIAA0001–KIAA0040) deduced by analysis of randomly sampled cDNA clones from human immature myeloid cell line KG–1," DNA Research, 1(1):27–35, 1994.
Stengel et al., "Different chromosomal localization of two adenylyl cyclae genes expressed in human brain," Hum. Genet., 90:126–130, 1992.
Haber et al., "Chromosomal mapping of human adenylyl cyclase genes type III, type V and type VI," Hum. Genet., 94(1):69–73, 1994.
Holmer et al., "Increase of adenylyl cyclase type V mRNA in human end–stage heart failure. G protein β–subunit mRNA is decreased in ischemic heart disease," European Heart Journal, 16:113, suppl. N, 1995.
Katsushika et al., "Cloning and characterization of a sixth adenylyl cyclase isoform: types V and VI constitute a subgroup within the mammalian adenylyl cyclase family," Proc. Natl. Acad. Sci. USA, 89(18):8774–8778, 1992.
Yoshimura et al., "Cloning and expression of a $Ca^{2+}$–inhibitable adenylyl cyclase from NCB–20 cells," Proc. Natl. Acad. Sci. USA, 89(15):6716–6720, 1992.

* cited by examiner

*Primary Examiner*—Ponnathapuachuta Murthy
*Assistant Examiner*—Kathleen Kerr
(74) *Attorney, Agent, or Firm*—Morgan, Lewis & Bockius LLP

(57) ABSTRACT

A DNA sequence encoding a human type V adenylyl cyclase is described. The amino acid sequence of the adenylyl cyclase is also described. This adenylyl cyclase is expressed at increased levels in heart and brain tissue, relative to other tissues.

14 Claims, 8 Drawing Sheets

FIG. IA

```
GCTGCAGCGC AGGGCCCCGG GCCGCCCCCG ACGTGTGACC CTAGCCTGGT    50
CGACGTCGCG TCCCGGGCC  CGGCGGGGC  TGCACACTGG GATCGGACCA

CCCCCTGCTC GGCCGTCCGC CCTCCCTTG  GAGACCCCG  GCCCGGCTTC   100
GGGGACGAG  CCGGCAGGCG GGAGGGGAAC CTCTGGGGGC CGGGCCGAAG

CGGGGGAGGA GGAAGGAGAC GACGAGGCCG AGGGGGGGAT GTCCGGCTCC   150
GCCCCCTCCT CCTTCCTCTG CTGCTCCGGC TCCCCCCCTA CAGGCCGAGG
                                          Me tSerGlySer

AAAAGCGTGA GCCCCCCGGG CTACGCGGCG CAGAAGACTG CGGCGCCGGC   200
TTTTCGCACT CGGGGGGCCC GATGCGCCGC GTCTTCTGAC GCCGCGGCCG
LysSerValS erProProGl yTyrAlaAla GlnLysThrA laAlaProAl

GCCCCGGGGA GGCCCCGAAC ACCGCTCTGC GTGGGCGAG  GCCGATTCCC   250
CGGGGCCCCT CCGGGGCTTG TGGCGAGACG CACCCCGCTC CGGCTAAGGG
aProArgGly GlyProGluH isArgSerAl aTrpGlyGlu AlaAspSerA

GCGCGAATGG CTACCCCCAT GCCCCCGGGG GTTCTGCCCG CGGCTCCACC   300
CGCGCTTACC GATGGGGGTA CGGGGGCCCC CAAGACGGGC GCCGAGGTGG
rgAlaAsnGl yTyrProHis AlaProGlyG lySerAlaAr gGlySerThr

AAGAAACCCG GGGGGGCGGT GACCCCGCAG CAGCAGCAGC GCCTGGCCAG   350
TTCTTTGGGC CCCCCCGCCA CTGGGGCGTC GTCGTCGTCG CGGACCGGTC
LysLysProG lyGlyAlaVa lThrProGln GlnGlnGlnA rgLeuAlaSe

CCGCTGGCGC AGCGACGACG ACGACGATCC TCCGCTGAGC GGTGACGACC   400
GGCGACCGCG TCGCTGCTGC TGCTGCTAGG AGGCGACTCG CCACTGCTGG
rArgTrpArg SerAspAspA spAspAspPr oProLeuSer GlyAspAspP

CCCTGGCCGG GGGCTTCGGC TTCAGCTTCC GCTCCAAGTC CGCCTGGCAG   450
GGGACCGGCC CCCGAAGCCG AAGTCGAAGG CGAGGTTCAG GCGGACCGTC
roLeuAlaGl yGlyPheGly PheSerPheA rgSerLysSe rAlaTrpGln

GAGCGCGGCG GCGACGACTG CGGTCGCGGC AGCCGCCGGC AGCGGCGGGG   500
CTCGCGCCGC CGCTGCTGAC GCCAGCGCCG TCGGCGGCCG TCGCCGCCCC
GluArgGlyG lyAspAspCy sGlyArgGly SerArgArgG lnArgArgGl

CGCGGCCAGC GGGGCAGCA  CCCGGGCGCC CCCTGCGGGC GGCGGCGGCG   550
GCGCCGGTCG CCCCCGTCGT GGGCCCGCGG GGGACGCCCG CCGCCGCCGC
yAlaAlaSer GlyGlySerT hrArgAlaPr oProAlaGly GlyGlyGlyG

GCTCGGCGGC GGCGGCTGCC TCGGCGGGCG GACGGAGGT  GGCCCTCGC    600
CGAGCCGCCG CCGCCGACGG AGCCGCCCGC CCTGCCTCCA CCGGGAGCG
lySerAlaAl aAlaAlaAla SerAlaGlyG lyThrGluVa lArgProArg
```

FIG. 1B

```
TCGGTGGAGG TGGGTCTGGA GGAGCGGCGG GGCAAGGGGC GCGCGGCCGA    650
AGCCACCTCC ACCCAGACCT CCTCGCCGCC CCGTTCCCCG CGCGCCGGCT
SerValGluV alGlyLeuGl uGluArgArg GlyLysGlyA rgAlaAlaAs

CGAGCTGGAG GCCGGCGCCG TCGAGGGCGG CGAGGGGTCC GGGGATGGCG    700
GCTCGACCTC CGGCCGCGGC AGCTCCCGCC GCTCCCCAGG CCCCTACCGC
pGluLeuGlu AlaGlyAlaV alGluGlyGl yGluGlySer GlyAspGlyG

GCAGCTCGGC GGACTCGGGC TCGGCGCGG GGCCCGGCGC GGTGCTGTCC    750
CGTCGAGCCG CCTGAGCCCG AGCCCGCGCC CCGGGCCGCG CCACGACAGG
lySerSerAl aAspSerGly SerGlyAlaG lyProGlyAl aValLeuSer

CTGGGCGCCT GCTGCCTGGC GTTGCTGCAG ATATTCCGCT CCAAGAAGTT    800
GACCCGCGGA CGACGGACCG CAACGACGTC TATAAGGCGA GGTTCTTCAA
LeuGlyAlaC ysCysLeuAl aLeuLeuGln IlePheArgS erLysLysPh

CCCGTCGGAC AAACTGGAGC GGCTGTACCA GCGCTACTTC TTCCGCCTGA    850
GGGCAGCCTG TTTGACCTCG CCGACATGGT CGCGATGAAG AAGGCGGACT
eProSerAsp LysLeuGluA rgLeuTyrGl nArgTyrPhe PheArgLeuA

ACCAGAGCAG CCTCACCATG CTCATGGCCG TGCTGGTGCT CGTGTGCCTG    900
TGGTCTCGTC GGAGTGGTAC GAGTACCGGC ACGACCACGA GCACACGGAC
snGlnSerSe rLeuThrMet LeuMetAlaV alLeuValLe uValCysLeu

GTCATGTTGG CCTTCCACGC GGCGCGGCCC CCGCTCCAGC TGCCCTACCT    950
CAGTACAACC GGAAGGTGCG CCGCGCCGGG GGCGAGGTCG ACGGGATGGA
ValMetLeuA laPheHisAl aAlaArgPro ProLeuGlnL euProTyrLe

GGCCGTGCTG GCGGCCGCCG TCGGCGTGAT CCTCATCATG GCTGTGCTTT    1000
CCGGCACGAC CGCCGGCGGC AGCCGCACTA GGAGTAGTAC CGACACGAAA
uAlaValLeu AlaAlaAlaV alGlyValIl eLeuIleMet AlaValLeuC

GCAACCGCGC CGCCTTCCAC CAGGACCACA TGGGCCTGGC CTGCTATGCG    1050
CGTTGGCGCG GCGGAAGGTG GTCCTGGTGT ACCCGGACCG GACGATACGC
ysAsnArgAl aAlaPheHis GlnAspHisM etGlyLeuAl aCysTyrAla

CTCATCGCCG TGGTGCTGGC CGTCCAGGTG GTGGGCCTGC TGCTGCCGCA    1100
GAGTAGCGGC ACCACGACCG GCAGGTCCAC CACCCGGACG ACGACGGCGT
LeuIleAlaV alValLeuAl aValGlnVal ValGlyLeuL euLeuProGl

GCCACGCAGC GCCTCTGAGG GCATCTGGTG GACCGTGTTC TTCATCTACA    1150
CGGTGCGTCG CGGAGACTCC CGTAGACCAC CTGGCACAAG AAGTAGATGT
nProArgSer AlaSerGluG lyIleTrpTr pThrValPhe PheIleTyrT

CCATCTACAC GCTGCTGCCC GTGCGCATGC GGGCCGCAGT GCTCAGCGGG    1200
GGTAGATGTG CGACGACGGG CACGCGTACG CCCGGCGTCA CGAGTCGCCC
hrIleTyrTh rLeuLeuPro ValArgMetA rgAlaAlaVa lLeuSerGly
```

FIG. IC

```
GTGCTCCTGT CCGCCCTCCA CCTGGCCATC GCCCTGCGCA CCAACGCCCA  1250
CACGAGGACA GGCGGGAGGT GGACCGGTAG CGGGACGCGT GGTTGCGGGT
ValLeuLeuS erAlaLeuHi sLeuAlaIle AlaLeuArgT hrAsnAlaGl

GGACCAGTTC CTGCTGAAGC AGCTTGTCTC CAATGTTCTC ATTTTCTCCT  1300
CCTGGTCAAG GACGACTTCG TCGAACAGAG GTTACAAGAG TAAAAGAGGA
nAspGlnPhe LeuLeuLysG lnLeuValSe rAsnValLeu IlePheSerC

GCACCAACAT CGTGGGTGTC TGCACCCACT ATCCGGCTGA GGTCTCCCAG  1350
CGTGGTTGTA GCACCCACAG ACGTGGGTGA TAGGCCGACT CCAGAGGGTC
ysThrAsnIl eValGlyVal CysThrHisT yrProAlaGl uValSerGln

AGACAGGCTT TCCAGGAGAC CCGAGAGTGC ATCCAGGCGC GGCTCCACTC  1400
TCTGTCCGAA AGGTCCTCTG GGCTCTCACG TAGGTCCGCG CCGAGGTGAG
ArgGlnAlaP heGlnGluTh rArgGluCys IleGlnAlaA rgLeuHisSe

GCAGCGGGAG AACCAGCAGC AGGAACGGCT CCTGCTGTCT GTCCTTCCCC  1450
CGTCGCCCTC TTGGTCGTCG TCCTTGCCGA GGACGACAGA CAGGAAGGGG
rGlnArgGlu AsnGlnGlnG lnGluArgLe uLeuLeuSer ValLeuProA

GTCATGTTGC CATGGAGATG AAAGCAGACA TCAACGCCAA GCAGGAGGAT  1500
CAGTACAACG GTACCTCTAC TTTCGTCTGT AGTTGCGGTT CGTCCTCCTA
rgHisValAl aMetGluMet LysAlaAspI leAsnAlaLy sGlnGluAsp

ATGATGTTCC ATAAGATTTA CATCCAGAAA CATGACAACG TGAGCATCCT  1550
TACTACAAGG TATTCTAAAT GTAGGTCTTT GTACTGTTGC ACTCGTAGGA
MetMetPheH isLysIleTy rIleGlnLys HisAspAsnV alSerIleLe

GTTTGCTGAC ATCGAGGGCT TCACCAGCCT GGCGTCCCAG TGCACTGCAC  1600
CAAACGACTG TAGCTCCCGA AGTGGTCGGA CCGCAGGGTC ACGTGACGTG
uPheAlaAsp IleGluGlyP heThrSerLe uAlaSerGln CysThrAlaG

AGGAACTGGT CATGACCCTC AACGAGCTCT TCGCCCGCTT TGACAAGCTG  1650
TCCTTGACCA GTACTGGGAG TTGCTCGAGA AGCGGGCGAA ACTGTTCGAC
lnGluLeuVa lMetThrLeu AsnGluLeuP heAlaArgPh eAspLysLeu

GCCGCAGAGA ATCACTGTTT ACGTATTAAG ATCCTTGGGG ATTGTTATTA  1700
CGGCGTCTCT TAGTGACAAA TGCATAATTC TAGGAACCCC TAACAATAAT
AlaAlaGluA snHisCysLe uArgIleLys IleLeuGlyA spCysTyrTy

CTGCGTCTCG GGGCTGCCTG AAGCAAGGGC TGACCACGCC CACTGCTGTG  1750
GACGCAGAGC CCCGACGGAC TTCGTTCCCG ACTGGTGCGG GTGACGACAC
rCysValSer GlyLeuProG luAlaArgAl aAspHisAla HisCysCysV

TGGAGATGGG CATGGACATG ATCGAGGCCA TCTCGTTGGT CCGGGAGGTG  1800
ACCTCTACCC GTACCTGTAC TAGCTCCGGT AGAGCAACCA GGCCCTCCAC
alGluMetGl yMetAspMet IleGluAlaI leSerLeuVa lArgGluVal
```

FIG. ID

```
ACAGGGGTGA  ACGTGAACAT  GCGTGTGGGA  ATTCACAGCG  GGCGAGTACA  1850
TGTCCCCACT  TGCACTTGTA  CGCACACCCT  TAAGTGTCGC  CCGCTCATGT
ThrGlyValA  snValAsnMe  tArgValGly  IleHisSerG  lyArgValHi

CTGCGGTGTC  CTTGGTCTCA  GGAAGTGGCA  GTTCGACGTC  TGGTCTAACG  1900
GACGCCACAG  GAACCAGAGT  CCTTCACCGT  CAAGCTGCAG  ACCAGATTGC
sCysGlyVal  LeuGlyLeuA  rgLysTrpGl  nPheAspVal  TrpSerAsnA

ATGTCACGCT  AGCCAACCAC  ATGGAGGCTG  GCGGCAAGGC  AGGACGCATC  1950
TACAGTGCGA  TCGGTTGGTG  TACCTCCGAC  CGCCGTTCCG  TCCTGCGTAG
spValThrLe  uAlaAsnHis  MetGluAlaG  lyGlyLysAl  aGlyArgIle

CACATCACCA  AGGCTACACT  CAACTACCTG  AATGGGGACT  ACGAGGTGGA  2000
GTGTAGTGGT  TCCGATGTGA  GTTGATGGAC  TTACCCCTGA  TGCTCCACCT
HisIleThrL  ysAlaThrLe  uAsnTyrLeu  AsnGlyAspT  yrGluValGl

GCCAGGCTGT  GGGGGCGAGC  GCAACGCCTA  CCTCAAGGAG  CACAGTATCG  2050
CGGTCCGACA  CCCCCGCTCG  CGTTGCGGAT  GGAGTTCCTC  GTGTCATAGC
uProGlyCys  GlyGlyGluA  rgAsnAlaTy  rLeuLysGlu  HisSerIleG

AGACCTTCCT  CATCCTGCGC  TGCACCCAGA  AGCGGAAAGA  AGAGAAGGCC  2100
TCTGGAAGGA  GTAGGACGCG  ACGTGGGTCT  TCGCCTTTCT  TCTCTTCCGG
luThrPheLe  uIleLeuArg  CysThrGlnL  ysArgLysGl  uGluLysAla

ATGATCGCCA  AGATGAACCG  CCAGAGAACC  AACTCCATCG  GCACAACCC   2150
TACTAGCGGT  TCTACTTGGC  GGTCTCTTGG  TTGAGGTAGC  CCGTGTTGGG
MetIleAlaL  ysMetAsnAr  gGlnArgThr  AsnSerIleG  lyHisAsnPr

ACCACACTGG  GGGGCTGAGC  GCCCCTTCTA  CAACCACCTG  GGTGGCAACC  2200
TGGTGTGACC  CCCCGACTCG  CGGGGAAGAT  GTTGGTGGAC  CCACCGTTGG
oProHisTrp  GlyAlaGluA  rgProPheTy  rAsnHisLeu  GlyGlyAsnG

AGGTGTCCAA  GGAGATGAAG  CGGATGGGCT  TTGAAGACCC  CAAGGACAAG  2250
TCCACAGGTT  CCTCTACTTC  GCCTACCCGA  AACTTCTGGG  GTTCCTGTTC
lnValSerLy  sGluMetLys  ArgMetGlyP  heGluAspPr  oLysAspLys

AACGCCCAGG  AGAGTGCGAA  CCCTGAGGAT  GAAGTGGATG  AGTTTCTGGG  2300
TTGCGGGTCC  TCTCACGCTT  GGGACTCCTA  CTTCACCTAC  TCAAAGACCC
AsnAlaGlnG  luSerAlaAs  nProGluAsp  GluValAspG  luPheLeuGl

CCGTGCCATT  GACGCCAGGA  GCATTGATAG  GCTTCGGTCT  GAGCACGTCC  2350
GGCACGGTAA  CTGCGGTCCT  CGTAACTATC  CGAAGCCAGA  CTCGTGCAGG
yArgAlaIle  AspAlaArgS  erIleAspAr  gLeuArgSer  GluHisValA

GCAAGTTCCT  CCTGACCTTC  AGGGAGCCTG  ACTTAGAGAA  GAAGTACTCC  2400
CGTTCAAGGA  GGACTGGAAG  TCCCTCGGAC  TGAATCTCTT  CTTCATGAGG
rgLysPheLe  uLeuThrPhe  ArgGluProA  spLeuGluLy  sLysTyrSer
```

FIG. IE

```
AAGCAGGTAG ACGACCGATT TGGTGCCTAT GTGGCGTGTG CCTCGCTCGT 2450
TTCGTCCATC TGCTGGCTAA ACCACGGATA CACCGCACAC GGAGCGAGCA
LysGlnValA spAspArgPh eGlyAlaTyr ValAlaCysA laSerLeuVa

CTTCCTCTTC ATCTGCTTTG TCCAGATCAC CATCGTGCCC CACTCCATAT 2500
GAAGGAGAAG TAGACGAAAC AGGTCTAGTG GTAGCACGGG GTGAGGTATA
lPheLeuPhe IleCysPheV alGlnIleTh rIleValPro HisSerIleP

TCATGCTCAG CTTCTACCTG ACCTGTTCCC TGCTGCTGAC CTTGGTGGTG 2550
AGTACGAGTC GAAGATGGAC TGGACAAGGG ACGACGACTG GAACCACCAC
heMetLeuSe rPheTyrLeu ThrCysSerL euLeuLeuTh rLeuValVal

TTTGTGTCTG TGATCTACTC CTGCGTAAAG CTCTTCCCCT CCCCACTGCA 2600
AAACACAGAC ACTAGATGAG GACGCATTTC GAGAAGGGGA GGGGTGACGT
PheValSerV alIleTyrSe rCysValLys LeuPheProS erProLeuGl

GACCCTCTCC AGGAAGATCG TGCGGTCCAA GATGAACAGC ACCCTGGTTG 2650
CTGGGAGAGG TCCTTCTAGC ACGCCAGGTT CTACTTGTCG TGGGACCAAC
nThrLeuSer ArgLysIleV alArgSerLy sMetAsnSer ThrLeuValG

GGGTGTTCAC CATCACCCTG GTGTTCCTGG CGGCTTTTGT CAACATGTTC 2700
CCCACAAGTG GTAGTGGGAC CACAAGGACC GCCGAAAACA GTTGTACAAG
lyValPheTh rIleThrLeu ValPheLeuA laAlaPheVa lAsnMetPhe

ACGTGCAACT CCAGGGACCT GCTGGGCTGC TTGGCACAGG AGCACAACAT 2750
TGCACGTTGA GGTCCCTGGA CGACCCGACG AACCGTGTCC TCGTGTTGTA
ThrCysAsnS erArgAspLe uLeuGlyCys LeuAlaGlnG luHisAsnIl

CAGCGCGAGC CAGGTCAACG CGTGTCACGT GGCGGAGTCG GCCGTCAACT 2800
GTCGCGCTCG GTCCAGTTGC GCACAGTGCA CCGCCTCAGC CGGCAGTTGA
eSerAlaSer GlnValAsnA laCysHisVa lAlaGluSer AlaValAsnT

ACAGCCTGGG CGATGAGCAG GGCTTCTGTG GCAGCCCCTG GCCCAACTGC 2850
TGTCGGACCC GCTACTCGTC CCGAAGACAC CGTCGGGGAC CGGGTTGACG
yrSerLeuGl yAspGluGln GlyPheCysG lySerProTr pProAsnCys

AACTTCCCCG AGTACTTCAC CTACAGCGTG CTGCTCAGCC TGCTGGCCTG 2900
TTGAAGGGGC TCATGAAGTG GATGTCGCAC GACGAGTCGG ACGACCGGAC
AsnPheProG luTyrPheTh rTyrSerVal LeuLeuSerL euLeuAlaCy

CTCCGTGTTC CTGCAGATCA GCTGCATCGG GAAGCTGGTG CTCATGCTGG 2950
GAGGCACAAG GACGTCTAGT CGACGTAGCC CTTCGACCAC GAGTACGACC
sSerValPhe LeuGlnIleS erCysIleGl yLysLeuVal LeuMetLeuA

CCATCGAGCT CATCTACGTG CTCATCGTGG AGGTGCCAGG TGTCACGCTC 3000
GGTAGCTCGA GTAGATGCAC GAGTAGCACC TCCACGGTCC ACAGTGCGAG
laIleGluLe uIleTyrVal LeuIleValG luValProGl yValThrLeu
```

FIG. IF

```
TTCGACAACG CCGACCTGCT GGTCACCGCC AACGCCATAG ACTTCTTCAA 3050
AAGCTGTTGC GGCTGGACGA CCAGTGGCGG TTGCGGTATC TGAAGAAGTT
PheAspAsnA laAspLeuLe uValThrAla AsnAlaIleA spPhePheAs

CAACGGGACC TCCCAGTGCC CTGAGCATGC AACCAAGGTG GCATTGAAGG 3100
GTTGCCCTGG AGGGTCACGG GACTCGTACG TTGGTTCCAC CGTAACTTCC
nAsnGlyThr SerGlnCysP roGluHisAl aThrLysVal AlaLeuLysV

TGGTGACGCC CATCATCATC TCAGTCTTTG TGCTGGCCCT GTACCTGCAC 3150
ACCACTGCGG GTAGTAGTAG AGTCAGAAAC ACGACCGGGA CATGGACGTG
alValThrPr oIleIleIle SerValPheV alLeuAlaLe uTyrLeuHis

GCCCAGCAGG TGGAGTCCAC TGCCCGCCTC GACTTCCTCT GGAAACTGCA 3200
CGGGTCGTCC ACCTCAGGTG ACGGGCGGAG CTGAAGGAGA CCTTTGACGT
AlaGlnGlnV alGluSerTh rAlaArgLeu AspPheLeuT rpLysLeuGl

GGCCACAGAG GAGAAAGAGG AGATGGAGGA GCTGCAGGCC TACAACCGGC 3250
CCGGTGTCTC CTCTTTCTCC TCTACCTCCT CGACGTCCGG ATGTTGGCCG
nAlaThrGlu GluLysGluG luMetGluGl uLeuGlnAla TyrAsnArgA

GGCTGCTGCA CAACATCCTG CCCAAGGACG TGGCCGCTCA CTTCCTGGCC 3300
CCGACGACGT GTTGTAGGAC GGGTTCCTGC ACCGGCGAGT GAAGGACCGG
rgLeuLeuHi sAsnIleLeu ProLysAspV alAlaAlaHi sPheLeuAla

CGCGAGCGGC GCAATGATGA GCTCTACTAT CAGTCCTGTG AGTGTGTGGC 3350
GCGCTCGCCG CGTTACTACT CGAGATGATA GTCAGGACAC TCACACACCG
ArgGluArgA rgAsnAspGl uLeuTyrTyr GlnSerCysG luCysValAl

GGTCATGTTC GCCTCCATCG CCAACTTCTC CGAGTTCTAC GTTGAGCTGG 3400
CCAGTACAAG CGGAGGTAGC GGTTGAAGAG GCTCAAGATG CAACTCGACC
aValMetPhe AlaSerIleA laAsnPheSe rGluPheTyr ValGluLeuG

AGGCCAACAA CGAGGGTGTC GAGTGCCTGC GGCTACTCAA TGAGATCATC 3450
TCCGGTTGTT GCTCCCACAG CTCACGGACG CCGATGAGTT ACTCTAGTAG
luAlaAsnAs nGluGlyVal GluCysLeuA rgLeuLeuAs nGluIleIle

GCTGACTTTG ATGAGATCAT CAGCGAGGAT CGGTTCCGGC AGCTGGAGAA 3500
CGACTGAAAC TACTCTAGTA GTCGCTCCTA GCCAAGGCCG TCGACCTCTT
AlaAspPheA spGluIleIl eSerGluAsp ArgPheArgG lnLeuGluLy

GATCAAGACC ATCGGCAGCA CCTACATGGC TGCCTCCGGC CTCAACGACT 3550
CTAGTTCTGG TAGCCGTCGT GGATGTACCG ACGGAGGCCG GAGTTGCTGA
sIleLysThr IleGlySerT hrTyrMetAl aAlaSerGly LeuAsnAspS

CTACCTACGA CAAGGTGGGC AAGACCCACA TCAAGGCACT GGCCGACTTT 3600
GATGGATGCT GTTCCACCCG TTCTGGGTGT AGTTCCGTGA CCGGCTGAAA
erThrTyrAs pLysValGly LysThrHisI leLysAlaLe uAlaAspPhe
```

FIG. IG

```
GCCATGAAGC TGATGGACCA GATGAAGTAC ATCAATGAGC ACTCCTTCAA  3650
CGGTACTTCG ACTACCTGGT CTACTTCATG TAGTTACTCG TGAGGAAGTT
AlaMetLysL euMetAspGl nMetLysTyr IleAsnGluH isSerPheAs

CAACTTCCAG ATGAAGATCG GCTCAACAT CGGCCCCGTG GTGGCCGGGG    3700
GTTGAAGGTC TACTTCTAGC CCGAGTTGTA GCCGGGGCAC CACCGGCCCC
nAsnPheGln MetLysIleG lyLeuAsnIl eGlyProVal ValAlaGlyV

TGATAGGGGC ACGAAAGCCT CAGTACGACA TCTGGGGCAA TACCGTGAAC    3750
ACTATCCCCG TGCTTTCGGA GTCATGCTGT AGACCCCGTT ATGGCACTTG
alIleGlyAl aArgLysPro GlnTyrAspI leTrpGlyAs nThrValAsn

GTGGCCAGCC GCATGGACAG CACCGGTGTA CCCGACCGCA TCCAGGTCAC    3800
CACCGGTCGG CGTACCTGTC GTGGCCACAT GGGCTGGCGT AGGTCCAGTG
ValAlaSerA rgMetAspSe rThrGlyVal ProAspArgI leGlnValTh

CACAGACATG TACCAGGTGC TGGCTGCCAA CACGTACCAG CTGGAGTGCC    3850
GTGTCTGTAC ATGGTCCACG ACCGACGGTT GTGCATGGTC GACCTCACGG
rThrAspMet TyrGlnValL euAlaAlaAs nThrTyrGln LeuGluCysA

GGGGCGTGGT CAAGGTCAAG GGCAAAGGCG AGATGATGAC CTACTTCCTC    3900
CCCCGCACCA GTTCCAGTTC CCGTTTCCGC TCTACTACTG GATGAAGGAG
rgGlyValVa lLysValLys GlyLysGlyG luMetMetTh rTyrPheLeu

AATGGAGGGC CCCCGCTCAG TTAGCAGCTG TTGGCCAATG GTGCCAGGCA    3950
TTACCTCCCG GGGGCGAGTC AATCGTCGAC AACCGGTTAC CACGGTCCGT
AsnGlyGlyP roProLeuSe r

GCCTGGCCTC CAGAGGCATG GAAGCAGCTT CTCTGTGTGC CGGGGGTGGC    4000
CGGACCGGAG GTCTCCGTAC CTTCGTCGAA GAGACACACG GCCCCCACCG

GGGGAAGCCA TGCTCCAGCC CGCAGGGCTG CGCTGCTGAG ATTTTCCACT    4050
CCCCTTCGGT ACGAGGTCGG GCGTCCCGAC GCGACGACTC TAAAAGGTGA

TGGACTCCAG AGCAGCTTCT GCCTTTGCTG GTGGGCAGCG GCCTCTGTCC    4100
ACCTGAGGTC TCGTCGAAGA CGGAAACGAC CACCCGTCGC CGGAGACAGG

CAGGCCCCGG GGTGCCAGCG TCCTGCGAGC ACCCAGCTGA CCAAAGATGT    4150
GTCCGGGGCC CCACGGTCGC AGGACGCTCG TGGGTCGACT GGTTTCTACA

TTCCCTCTGT AGAAGACTCT GCTAGACTGG GTCTGAAGCT TGAGTTTTCT    4200
AAGGGAGACA TCTTCTGAGA CGATCTGACC CAGACTTCGA ACTCAAAAGA
```

FIG. IH

```
AACAGGTGCT GCTGCACAGG TGGAAAGGAG CCGTGGGAAT GTGTGTGTGG    4250
TTGTCCACGA CGACGTGTCC ACCTTTCCTC GGCACCCTTA CACACACACC

CACGGCCCAG ACAAGGGCAG GGCTGAGGGG CCTCCGACTC AGCTGGGGGT    4300
GTGCCGGGTC TGTTCCCGTC CCGACTCCCC GGAGGCTGAG TCGACCCCCA

AGACGGGCTC GAATGTGGCC TGGAGAGCC  TAGGGGCCC  CAGGGGTCTG    4350
TCTGCCCGAG CTTACACCGG ACCCTCTCGG ATCCCCCGGG GTCCCCAGAC

CTTTTCTATG TGAGCCTTTA AACTTCAGAC AGGCCACCAC CCTGCACCTG    4400
GAAAAGATAC ACTCGGAAAT TTGAAGTCTG TCCGGTGGTG GGACGTGGAC

CAGGGGCTTT GGCACAGGAG TGCTGGCTTT GGAGGGACTG TGGCCTTCAT    4450
GTCCCCGAAA CCGTGTCCTC ACGACCGAAA CCTCCCTGAC ACCGGAAGTA

CGTGGTCCTC TGCCCACACC TCCACGCACA CAGACAGTGC CCTAGGAGGG    4500
GCACCAGGAG ACGGGTGTGG AGGTGCGTGT GTCTGTCACG GGATCCTCCC

AAACAGAACT AATTACGAGG GGG                                4523
TTTGTCTTGA TTAATGCTCC CCC
```

POLYNUCLEOTIDES ENCODING A TYPE V ADENYLYL CYCLASE

This is a continuation of copending application(s) International Application No. PCT/US98/13540 filed on Jul. 1, 1998 which designated the U.S. and which is a continuation to U.S. application Ser. No. 08/886,362 filed on Jul. 1, 1997 now abandoned and to U.S. provisional Application No. 60/070,901 filed Jul. 1, 1997, all of which are incorporated herewith in their entirety.

FIELD OF THE INVENTION

This invention relates to DNA encoding a human adenylyl cyclase. This invention also relates to the adenylyl cyclase encoded by that DNA. Referred to herein as the human type V adenylyl cyclase (hAC5) polypeptide, this enzyme can be used as a tool to screen for agonists and antagonists that can either stimulate or inhibit type V adenylyl cyclase activity. Such compounds have therapeutic utility in treating (1) diseases that are caused by aberrant activity of this enzyme and (2) diseases whose symptoms can be ameliorated by stimulating or inhibiting the activity of type V adenylyl cyclase.

The present invention also relates to the isolated entire human gene encoding the human type V adenylyl cyclase, methods for the recombinant production of purified human type V adenylyl cyclase and the proteins made by these methods, antibodies against the whole human type V adenylyl cyclase or regions thereof, vectors, nucleotide probes, and host cells transformed by genes encoding polypeptides having human type V adenylyl cyclase activity, along with diagnostic and therapeutic uses for these various reagents.

BACKGROUND OF THE INVENTION

Adenylyl cyclases direct the intracellular synthesis of the primary second messenger, cyclic-3',5'-adenosine monophosphate (cAMP), by converting ATP to cAMP, principally in response to a diverse family of membrane spanning, G-protein coupled receptors, each activated by its own extracellular hormone or protease. Signal transduction for G-protein coupled receptors occurs through a coupled heterotrimeric G protein complex composed of the alpha ($G_a$), and beta/gamma ($G_{bg}$) subunits. Upon receptor stimulation, $G_a$ exchanges GTP for GDP, dissociates from both $G_{bg}$ and the receptor, and proceeds to directly regulate various effectors, including adenylyl cyclase. Multiple families of $G_a$ proteins have been identified, two of which are named for their effects on regulating adenylyl cyclase activity ($G_{as}$ family stimulates all adenylyl cyclases, while $G_{ai}$ family inhibits most but not all of the adenylyl cyclases). Each of these $G_a$ proteins has its own tissue distribution, and subset of coupled receptors, which favors receptor specific regulation of adenylyl cyclase.

Additional studies have suggested other means by which adenylyl cyclase activity may be regulated within tissues. This concept is derived from findings that a number of adenylyl cyclase isoforms exist, each with their own gene locus, distinct set of responses to intracellular signals and unique tissue distribution. To date, nine separate isoforms (Types I–IX) have been characterized, principally from rodents, each with its own regulatory properties and tissue specific distribution.

The structure of adenylyl cyclases has been greatly studied and the putative domains given standard nomenclature. Topographically, the adenylyl cyclase isoforms are similar, having two six-transmembrane spanning regions associated with an intracellular N-terminus, a large cytoplasmic loop (ICD III, more commonly referred to as "$C_1$") and an intracellular C-terminus (more commonly referred to as "$C_2$"). The transmembrane region between the N-terminus and the $C_1$ loop is commonly referred to as "M1". The M1 region has three extracellular domains (ECD I, II and III), two intracellular domains (ICD I and II) and six transmembrane domains (TM I, II, III, IV, V and VI). The region between the $C_1$ loop and the C-terminus is referred to as "M2". The M2 region has three extracellular domains (ECD IV, V and VI), two intracellular domains (ICD IV and V) and six transmembrane domains (TM VII, VIII, IX, X, XI and XII). The N-terminus is commonly divided into two regions, designated "$N_1$" and "$N_2$". The large $C_1$ cytoplasmic loop is also divided into two regions, a long "$C_{1a}$" region and a shorter "$C_{1b}$" region. Lastly, the C-terminus is divided into a long "$C_{2a}$" region and a shorter "$C_{2b}$" region. An extensive discussion of these regions can be found in Broach, et al., WO 95/30012, which is incorporated herein by reference. The amino acid sequence of the $C_{1a}$ and $C_{2a}$ regions are conserved among the different isoforms. On the other hand, the N-terminus, $C_{1b}$ and $C_{2b}$ regions show the most diversity among the various isoforms.

Based on sequence and functional similarities, these isoforms fall into six distinct classes of adenylyl cyclases. Type V is in the same class as type VI, showing sequence similarity even in the transmembrane regions where the greatest level of divergence is noted among the isoforms. Type V is expressed predominantly in heart and brain tissue. Type VI has a somewhat broader distribution but its dominant expression is also in heart and brain tissue. Type V, like type VI, has a relatively longer N-terminus and relatively shorter C-terminus, lacking the $C_{2b}$ region, than the other isoforms.

Diversity in activities, and differences in distribution and prevalence of adenylyl cyclase isoforms, may contribute to tissue specific regulation of cAMP levels. It is expected that by taking advantage of distinct structural and biochemical differences between different adenylyl cyclases, isoform specific or selective modulators can be discovered. This, in conjunction with knowledge of the proportion and distribution of each isoform in select tissues provides a means by which one can develop either tissue specific, or selective pharmacological agents since it is expected that isoform specific modulators would have tissue specificity related to the distribution of that isoform.

Key to the development of selective pharmacological agents is information pertaining to the tissue specific distribution and prevalence of each isoform. To date most of this information is available for isoform mRNA levels in a handful of non-human mammals, although some select mRNA (e.g. Type V) have been measured for many human tissues.

Acquiring information on protein isoform distribution in human tissues is considered an important aspect of pharmaceutical research in this area, since this could either strengthen existing target information or point to different isoforms, when compared with mRNA data To date, only three full length human adenylyl cyclase isoforms have been cloned: Type II adenylyl cyclase (Stengel, et al., *Hum. Genet.* 90:126–130 (1992)), Type VII adenylyl cyclase (Nomura, et al., *DNA Research* 1:27–35 (1994)) and Type VIII adenylyl cyclase (Defer, et al., *FEBS Letters* 351:109–113 (1994)).

Type V has been cloned from canine heart (Ishikawa, et al. *Jour. Biol. Chem.* 267(19):13553–13557 (1992) and Ishikawa, WO 93/05061). The human isoform has not been cloned until now.

SUMMARY OF THE INVENTION

One aspect of the invention is an isolated and purified human type V adenylyl cyclase (hAC5) polypeptide comprising the amino acid sequence of FIG. 1 (SEQ ID NO:2).

Another aspect of the invention is an isolated and purified nucleic acid encoding for the hAC5 polypeptide.

Yet another aspect of the invention is an isolated and purified nucleic acid comprising the nucleotide sequence of FIG. 1 (SEQ ID NO:1), which encodes a biologically active hAC5 polypeptide, or fragment thereof.

Still another aspect of the invention is an isolated and purified nucleic acid comprising the nucleotide sequence of FIG. 1 (SEQ ID NO:1), which encodes a biologically active soluble hAC5 peptide fragment.

Another aspect of the present invention also relates to the human gene encoding human type V adenylyl cyclase, which has both diagnostic and therapeutic uses as are described below. Included within this invention are proteins or peptides having substantial homology with proteins or peptides comprising the amino acid sequence of FIG. 1 or encoded by a gene having substantial homology with the nucleotide sequence of FIG. 1, and which exhibit the same characteristics of human type V adenylyl cyclase.

Yet another aspect of the invention is a method of producing hAC5 which comprises incorporating a nucleic acid having the nucleotide sequence of FIG. 1 (SEQ ID NO:1) into an expression vector, transforming a host cell with the vector and culturing the transformed host cell under conditions which result in expression of the gene.

BRIEF DESCRIPTION OF THE DRAWINGS

FIGS. 1(A–H) is the DNA (SEQ ID NO:1) and deduced amino acid sequence (SEQ ID NO:2) of human type V adenylyl cyclase. The entire coding sequence, as well as portions of the 5' and 3' untranslated sequences, are shown. The whole sequence was done bidirectionally twice by dideoxy sequencing method using Taq polymerase.

DETAILED DESCRIPTION OF THE INVENTION

Definitions

Before proceeding further with a description of the specific embodiments of the present invention, a number of terms will be defined:

The terms "substantially pure" and "isolated" are used herein to describe a protein that has been separated from the native contaminants or components that naturally accompany it. Typically, a monomeric protein is substantially pure when at least about 60 to 70% of a sample exhibits a single polypeptide backbone. Minor variants or chemical modifications typically share approximately the same polypeptide sequence. A substantially pure protein will typically comprise over about 85 to 90% of a protein sample, preferably will comprise at least about 95%, and more preferably will be over about 99% pure. Purity is typically measured on a polyacrylamide gel, with homogeneity determined by staining. For certain purposes, high resolution will be desired and HPLC or a similar means for purification utilized. However, for most purposes, a simple chromatography column or polyacrylamide gel will be used to determine purity. Whether soluble or membrane bound, the present invention provides for substantially pure preparations. Various methods for their isolation from biological material may be devised, based in part upon the structural and functional descriptions contained herein. In addition, a protein that is chemically synthesized or synthesized in a cellular system that is different from the cell from which it naturally originates, will be substantially pure. The term is also used to describe proteins and nucleic acids that have been synthesized in heterologous mammalian cells, bacterial cells such as E. coli and other prokaryotes.

As used herein, the terms "hybridization" (hybridizing) and "specificity" (specific for) in the context of nucleotide sequences are used interchangeably. The ability of two nucleotide sequences to hybridize to each other is based upon a degree of complementarity of the two nucleotide sequences, which in turn is based on the fraction of matched complementary nucleotide pairs. The more nucleotides in a given sequence that are complementary to another sequence, the greater the degree of hybridization of one to the other. The degree of hybridization also depends on the conditions of stringency which include temperature, solvent ratios, salt concentrations, and the like. In particular, "selective hybridization" pertains to conditions in which the degree of hybridization of a polynucleotide of the invention to its target would require complete or nearly complete complementarity. The complementarity must be sufficiently high so as to assure that the polynucleotide of the invention will bind specifically to the target relative to binding other nucleic acids present in the hybridization medium. With selective hybridization, complementarity will be 90–100%, preferably 95–100%, more preferably 100%.

"Stringent conditions" are those that (1) employ low ionic strength and high temperature for washing, for example, 0.015 M NaCl/0.0015 M sodium titrate/0.1% NaDodSO$_4$ at 50° C., or (2) employ during hybridization a denaturing agent such as formamide, for example, 50% (vol/vol) formamide with 0.1% bovine serum albumin ("BSA")/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×0.75 M NaCl and 0.075 M sodium citrate ("SSC"), 50 mM sodium phosphate (pH 6.8), 0.1% sodium pyrophosphate, 5×Denhardt's solution, sonicated salmon sperm DNA (50 mg/ml), 0.1% sodium dodecyl sulfate ("SDS"), and 10% dextran sulfate at 42° C., with washes at 42° C. in 0.2×SSC and 0.1% SDS.

"Isolated" nucleic acid will be nucleic acid that is identified and separated from contaminant nucleic acid encoding other polypeptides from the source of nucleic acid. The nucleic acid may be labeled for diagnostic and probe purposes, using any label known and described in the art as useful in connection with diagnostic assays.

Preferred Embodiments

The present invention relates to human type V adenylyl cyclase, which is referred to herein as "hAC5". FIG. 1 shows the DNA sequence of the clone encoding the hAC5 polypeptide along with the deduced amino acid sequence. As used herein, the terms "hAC5 polypeptide" or "hAC5 enzyme" refer to any adenylyl cyclase sharing a common biological activity with the human type V adenylyl cyclase contained in the clone described in Example 1. This "common biological activity" includes but is not limited to an effector function or cross-reactive antigenicity.

As indicated above, type V adenylyl cyclase is in the same isoform class as type VI, being expressed mainly in the heart and brain. As with the other known isoforms, type V adenylyl cyclase has a similar putative structure: six extracellular domains; five intracellular domains, four small ones and a large cytoplasmic loop; and intracellular amino and carboxy termini.

However, type V adenylyl cyclase, like type VI, is distinguishable over other adenylyl cyclase isoforms in that it has a larger N-terminus and a relatively shorter C-terminus as it lacks the $C_{2b}$ region. In the other mammalian isoforms (types I–IV and VI–IX), much of the membrane associated secondary structure is well conserved. Certain portions of the hAC5 polypeptide are similarly conserved.

The scope of the present invention is not limited to the exact sequence of the hAC5 cDNA set forth in FIG. 1 (SEQ ID NO: 1), or the use thereof. The invention contemplates certain modifications to the sequence, including deletions, insertions, and substitutions, such as are well known to those skilled in the art. For example, the invention contemplates replacing one or more codons in the cDNA sequence of FIG. 1, with codons that encode amino acids that are chemically equivalent to the amino acids in the native protein. Chemical equivalency is determined, for example, by one or more of the following characteristics: hydrophobicity or hydrophilicity, charge, size, whether the residue is cyclic or non-cyclic, aromatic or non-aromatic. So, for example, a codon encoding a neutral polar amino acid can be substituted with another codon that encodes a neutral polar residue, with the reasonable expectation of producing a biologically equivalent product.

Amino acid residues can be generally classified into four groups. Acidic residues are hydrophilic and have a negative charge due to loss of $H^+$ at physiological pH. Basic residues are also hydrophilic but have a positive charge due to association with $H^+$ at physiological pH. Neutral nonpolar residues are hydrophobic and are not charged at physiological pH. Neutral polar residues are hydrophilic and are not charged at physiological pH. Amino acid residues can be further classified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

Of the naturally occurring amino acids, aspartic acid and glutamic acid are acidic; arginine and lysine are basic and noncyclic; histidine is basic and cyclic; glycine, serine and cysteine are neutral, polar and small; alanine is neutral, nonpolar and small; threonine, asparagine and glutamine are neutral, polar, large and nonaromatic; tyrosine is neutral, polar, large and aromatic; valine, isoleucine, leucine and methionine are neutral, nonpolar, large and nonaromatic; and phenylalanine and tryptophan are neutral, nonpolar, large and aromatic. Proline, although technically neutral, nonpolar, large, cyclic and nonaromatic, is a special case due to its known effects on the secondary conformation of peptide chains, and is not, therefore, included in this defined group.

There are also commonly encountered amino acids, which are not encoded by the genetic code. These include, by way of example and not limitation: sarcosine, beta-alanine, 2,3-diamino propionic and alpha-aminisobutyric acid which are neutral, nonpolar and small; t-butylalanine, t-butylglycine, N-methylisoleucine, norleucine and cyclohexylalanine which are neutral, nonpolar, large and nonaromatic; ornithine which is basic and noncyclic; cysteic acid which is acidic; citrulline, acetyl lysine, and methionine sulfoxide which are neutral, polar, large and nonaromatic; and phenylglycine, 2-naphthylalanine, β-2-thienylalanine and 1,2,3,4-tetrahydroisoquinoline-3-carboxylic acid which are neutral, nonpolar, large and aromatic.

Ordinarily, the hAC5 polypeptide claimed herein will have an overall amino acid sequence having at least 75% amino acid sequence identity with the hAC5 sequence disclosed in FIG. 1, more preferably at least 80%, even more preferably at least 90%, and most preferably at least 95%. More particularly, the N-terminus, C1b and C2b regions of the hAC5 polypeptide or polypeptide fragment claimed herein, will have an amino acid sequence having at least 90%, and most preferably at least 95% amino acid sequence identity with the hAC5 sequence disclosed in FIG. 1. Identity or homology with a sequence is defined herein as the percentage of amino acid residues in the candidate sequence that are identical with the sequence of the hAC5 polypeptide, after aligning the sequences and introducing gaps, if necessary, to achieve the maximum percent homology, and not considering any conservative substitutions as part of the sequence identity. N-terminal, C-terminal or internal extensions, deletions, or insertions of the hAC5 sequence shall be construed as affecting homology.

Thus, the claimed hAC5 polypeptide that is the subject of this invention includes molecules having the hAC5 amino acid sequence; fragments thereof having a consecutive sequence of at least 10, 15, 20, 25, 30 or 40 amino acid residues from the hAC5 sequence of FIG. 1, which exhibits the hAC5 polypeptide characteristics; amino acid sequence variants of the hAC5 sequence of FIG. 1 wherein an amino acid residue has been inserted N- or C-terminal to, or within, (including parallel deletions) the hAC5 sequence or its fragments as defined above; amino acid sequence variants of the hAC5 sequence of FIG. 1 or its fragments as defined above which have been substituted by at least one residue, and which exhibit the hAC5 polypeptide characteristics. Of particular interest are those peptides corresponding to those regions where the hAC5 polypeptide is divergent from types I–IV and VI–IX.

Human type V adenylyl cyclase polypeptides include those containing predetermined mutations by, e.g., homologous recombination, site-directed or PCR mutagenesis; naturally occurring variants of the hAC5 polypeptide; derivatives of the hAC5 polypeptide or its fragments wherein the hAC5 or its fragments have been covalently modified by substitution, chemical, enzymatic, or other appropriate means with a moiety other than a naturally occurring amino acid (for example a detectable moiety such as an enzyme or radioisotope); glycosylation variants of the hAC5 (insertion of a glycosylation site or deletion of any glycosylation site by deletion, insertion or substitution of appropriate amino acid); and soluble forms of the hAC5 polypeptide or fragments thereof. This invention also includes tagging the hAC5 polypeptide, for example, for use in a diagnostic application. Types and methods of tagging are well known in the art, for example, the use of hexa-histidine tags.

Several regions of the Type V isoform are highly conserved with the other adenylyl cyclase isoforms. Accordingly, it is believed that most sequence modifications to the highly conserved regions such as the extracellular domains, transmembrane regions and short intracellular domains, including deletions and insertions, and substitutions in particular, are not expected to produce radical changes in the characteristics of the hAC5 polypeptide, distinct from those found with similar changes to other isoforms. However, when it is difficult to predict the exact effect of the sequence modification in advance of making the change, one skilled in the art will appreciate that the effect of any sequence modification will be evaluated by routine screening assays.

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^+_2$ and C-terminal $O^-$ at physiological pH are understood to be present though not necessarily specified and shown, either in specific examples or in generic formulas. Free functional groups on the side chains of the amino acid residues can also be modified by amidation, acylation or other substitution, which can, for example, change the solubility of the compounds without affecting their activity. All of the compounds of the invention, when an amino acid forms the C-terminus, may be in the form of the pharmaceutically acceptable salts or esters. Salts may be, for example, $Na^+$, $K^+$, $Ca^{+2}$, $Mg^{+2}$ and the like; the esters are generally those of alcohols of 1–6 carbons.

In all of the peptides of the invention, one or more amide linkages (—CO—NH—) may optionally be replaced with another linkage which is an isostere such as —CH$_2$NH—, —CH$_2$S—, —CH$_2$CH$_2$—, —CH=CH— (cis and trans), —COCH$_2$—, —CH(OH)CH$_2$— and —CH$_2$SO—. This replacement can be made by method known in the art. The following references describe preparation of peptide analogs which include these alterative-linking moieties: Spatola, *Vega Data* 1(3) "Peptide Backbone Modifications" (general review) (March 1983); Spatola, in "Chemistry and Biochemistry of Amino Acids Peptides and Proteins," B. Weinstein, eds., Marcel Dekker, New York, p. 267 (1983) (general review); Morley, J. S., *Trends Pharm Sci*, pp. 463–468 (general review) (1980); Hudson, et al., *Int J Pept Prot Res* 14:177–185 (—CH$_2$NH—, —CH$_2$CH$_2$—) (1979); Spatola, et al., *Life Sci* 38:1243–1249 (—CH$_2$—S) (1986); Hann, *J Chem Soc Perkin Trans I* 307–314 (—CH—CH—, cis and trans) (1982); Almquist, et al., *J Med Chem* 23:1392–1398 (—COCH$_2$—) (1980); Jennings-White, et al., *Tetrahedron Lett* 23:2533 (—COCH$_2$—) (1982); Szelke, et al., European Application EP 45665 (1982) CA:97:39405 (1982) (—CH(OH)CH$_2$—); Holladay, et al., *Tetrahedron Lett* 4:4401–4404 (—C(OH)CH$_2$—) (1983); and Hruby, *Life Sci* 31:189–199 (—CH$_2$—S—) (1982).

Human type V adenylyl cyclase peptides may be purified using techniques of classical protein chemistry, such as are well known in the art. For example, a lectin affinity chromatography step may be used, followed by a highly specific ligand affinity chromatography procedure that utilizes a ligand conjugated to biotin through the cysteine residues of the ligand. Alternately, the hexa-histidine tagged hAC5 polypeptide may be purified using nickel column chromatography.

One embodiment of the invention relates to recombinant materials associated with the production of the hAC5 polypeptide. One method of producing hAC5 comprises incorporating a nucleic acid having the nucleotide sequence of FIG. 1 (SEQ ID NO:1) into an expression vector, transforming a host cell with the vector and culturing the transformed host cell under conditions which result in expression of the gene. Suitable expression vectors include pc3hAC6.

Examples of host cells includes bacterial, viral, yeast, insect or mammalian cell lines. A preferred host cell is the human embryonic cell line referred to as "HEK-293".

The invention also contemplates the use of transfected cells that can be cultured so as to display or express hAC5 on its surface, thus providing an assay system for the interaction of materials with the native hAC5 where these cells or relevant fragments of hAC5 are used as a screening tool to evaluate the effect of various candidate compounds on hAC5 activity in vivo, as is described below. Another embodiment of the invention relates to recombinant materials associated with the production of soluble hAC5 fragments. These include transfected cells, such as *E. coli*, that can be cultured so as to express active portions of the hAC5 polypeptide, in particular the C1 and C2 (C-terminus) intracellular loops. These soluble fragments can be purified and reconstituted to obtain enzymatic activity. This has been demonstrated with like domains from other isoforms. See Whisnant, et al., *Proc. Natl. Acad. Sci.*:93:6621–6625 (1996). Such soluble fragments can also be used as a screening tool to evaluate the effect of various candidate compounds on hAC5 activity. Suitable cells for transfection include bacterial cells, insect cells such as Sf-9 cells, yeast cells and most mammalian cell lines.

Recombinant production of the hAC5 polypeptide involves using a nucleic acid sequence that encodes hAC5, as is set forth in FIG. 1, or its degenerate analogs. The nucleic acid can be prepared either by retrieving the native sequence, as described below, or by using substantial portions of the known native sequence as a probe, or it can be synthesized de novo using procedures that are well known in the art.

The nucleic acid may be ligated into expression vectors suitable for the desired host and then transformed into compatible cells. Suitable vectors suitable for use in transforming bacterial cells are well known in the art. Plasmids and bacteriophages, such as lambda phage, are commonly used as vectors for bacterial hosts such as *E. coli*. Virus vectors are suitable for use in mammalian and insect cells for expression of exogenous DNA. Mammalian cells are readily transformed with SV40 or polyoma virus; and insect cells in culture may be transformed with baculovirus expression vectors. Suitable yeast vector systems include yeast centromere plasmids, yeast episomal plasmids and yeast integrating plasmids. Alternatively, nucleic acids may be introduced directly into a host cell by techniques such as are well known in the art.

The cells are cultured under conditions favorable for the expression of the gene encoding the hAC5 polypeptide and cells displaying hAC5 on the surface are then harvested. Suitable eukaryotic host cells include mammalian cells, plant cells, yeast cells and insect cells. Suitable prokaryotic host cells, include bacterial cells such as *E. coli* and *Bacillus subtilis*, Chinese Hamster Ovary cells, COS cells, the rat-2 fibroblast cell line, the human embryonic kidney 293 cell line, and insect cell lines such as Sf-9.

This invention also relates to nucleic acids that encode or are complementary to a hAC5 polypeptide. These nucleic acids can then be used to produce the polypeptide in recombinant cell culture for diagnostic use or for potential therapeutic use. In still other aspects, the invention provides an isolated nucleic acid molecule encoding hAC5, either labeled or unlabeled, or a nucleic acid sequence that is complementary to, or hybridizes under stringent conditions to, a nucleic acid sequence encoding hAC5. The isolated nucleic acid molecule of the invention excludes nucleic acid sequences which encode, or are complementary to nucleic acid sequences encoding, other known adenylyl cyclase isoforms.

This invention also provides a replicable vector comprising a nucleic acid molecule encoding hAC5 operably linked to control sequences recognized by a host transformed by the vector; host cells transformed with the vector; and a method of using a nucleic acid molecule encoding hAC5 to effect the production of hAC5 on the cell surface or as soluble fragments, comprising expressing the nucleic acid molecule in a culture of the transformed host cells and recovered from the cells. The nucleic acid sequence is also useful in hybridization assays for hAC5-encoding nucleic acid molecules.

In still further embodiments of the invention, a method is described for producing hAC5 comprising inserting into the DNA of a cell containing the nucleic acid sequence encoding hAC5, a transcription modulatory element (such as an enhancer or a silencer) in sufficient proximity and orientation to the hAC5-coding sequence to influence transcription thereof, with an optional further step comprising culturing the cell containing the transcription modulatory element and the hAC5-encoding nucleic acid sequence.

This invention also covers a cell comprising a nucleic acid sequence encoding the hAC5 polypeptide and an exogenous transcription modulatory element in sufficient proximity and orientation to the above coding sequence to influence transcription thereof and a host cell containing the nucleic acid sequence encoding hAC5 operably linked to exogenous control sequences recognized by the host cell.

This invention provides a method for obtaining cells having increased or decreased transcription of the nucleic acid molecule encoding the hAC5 polypeptide, comprising: providing cells containing the nucleic acid molecule; introducing into the cells a transcription modulating element; and screening the cells for a cell in which the transcription of the nucleic acid molecule is increased or decreased.

Human adenylyl cyclase type V nucleic acids for use in the invention can be produced as follows. A hAC5 "nucleic acid" is defined as RNA or DNA that encodes the hAC5 polypeptide, or is complementary to nucleic acid sequence encoding hAC5, or hybridizes to such nucleic acid and remains stably bound to it under stringent conditions, or encodes a polypeptide sharing at least 75% sequence identity, preferably at least 80%, and more preferably at least 85%, with the deduced amino acid sequence shown in FIG. 1. It is typically at least about 10 nucleotides in length and preferably has hAC5 related biological or immunological activity. Specifically contemplated are genomic DNA, cDNA, mRNA and antisense molecules, as well as nucleic acids based on alternative backbone or including alternative bases whether derived from natural sources or synthesized.

Of particular interest is a hAC5 nucleic acid that encodes a full-length molecule, including but not necessarily the native signal sequence thereof. Nucleic acid encoding full-length protein is obtained by screening selected cDNA or genomic libraries using the deduced amino acid sequence disclosed herein for the first time, and, if necessary, using conventional primer extension procedures to secure DNA that is complete at its 5' coding end. Such a clone is readily identified by the presence of a start codon in reading frame with the original sequence.

DNA encoding an amino acid sequence variant of the hAC5 polypeptide is prepared as described below or by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of hAC5.

Techniques for isolating and manipulating nucleic acids are disclosed for example by the following documents: U.S. Pat. No. 5,030,576, U.S. Pat. No. 5,030,576 and International Patent Publications WO94/11504 and WO93/03162. See, also, Sambrook, et al., "Molecular Cloning: A Laboratory Manual", 2nd Edition, Cold Spring Harbor Press, Cold Spring Harbor, N.Y., 1989, and Ausubel, et al. "Current Protocols in Molecular Biology", Vol. 2, Wiley-Interscience, New York, 1987.

The isolation, recombinant production and characterization of the hAC5 polypeptide allows for the design of assay systems using hAC5. The availability of the isolated cells providing hAC5 on their surface and the availability of the recombinant DNA encoding hAC5 which permits display and expression of the enzyme on host cell surfaces, all makes such cells available as a valuable tool for evaluating the ability of candidate pharmaceuticals, both agonists and antagonists, to affect the activity of hAC5. In this manner, the invention is related to assay systems which utilize isolated or recombinantly produced hAC5 to screen for agonist and antagonist activity of candidate drugs. This assay is especially useful in assuring that these candidate therapeutic agents have the desired effect on hAC5. Determination of these properties is essential in evaluating the specificity of drugs for other adenylyl cyclase isoforms.

The host cells are typically animal cells, most typically mammalian cells. In order to be useful in the assays, the cells must have intracellular mechanisms which permit hAC5 to be displayed on the cell surface or to be expressed as soluble fragments. The animal host cells expressing the DNA encoding the hAC5 polypeptide or a fragment thereof are then cultured to effect the expression of the encoding nucleic acids so as to either 1) produce hAC5 display on the cell surface such that the cells can then be used directly in assays for assessment of a candidate drug to bind to or otherwise affect the activity of the enzyme, or 2) produce hAC5 as soluble fragments which can then be purified and reconstituted to obtain an enzymatically active compound useful in screening assays.

There are several possible strategies to identify compounds which affect hAC5 activity. Over expression of the hAC5 cDNA can provide a means for isolation of large quantities of crude membrane preparations from a stable cell line. HEK-293 cells have been found to be particularly useful for this purpose. In this system the measurable enzyme activity would be predominantly from expression of recombinant hAC5. A highly sensitive, reproducible, high throughput screening system is desirable, with enzyme activity detected in a 96 well, scintillation proximity-type assay to measure product formation (cAMP). There are numerous screening assays that can be utilized. For example, the basal (unstimulated) activity of hAC5 can be measured as a method of detecting both agonists and antagonists of the hAC5 enzyme. In addition, stimulation of the enzyme by its most relevant physiological activator, the heterotrimeric G protein subunit, $G_{\alpha s}$, can be assayed using activated (GTPgS bound) recombinant bovine $G_{\alpha s}$ (expressed and purified from bacteria), with the expectation that additional compounds may be identified which inhibit $G_{\alpha s}$ stimulation of the hAC5 polypeptide. Other stimulatory agents can also be used, such as forskolin or forskolin analogs. "Hits", i.e., compounds which affect hAC5, in any of these screens will be further evaluated in other assays to help focus on compounds which are relevant to the targeted isoform.

Another method of evaluating candidates as potential therapeutic agents typically involves a screening based approach such as a binding assay in which the candidate (such as a peptide or a small organic molecule) would be tested to measure if, or to what extent, it binds the catalytic subunit of the hAC5 enzyme. Preferably, a mammalian cell line that expresses recombinant hAC5 or plasma membrane preparations thereof, will be used in the assay. For example, a candidate antagonist competes for binding to hAC5 with either a labeled agonist or antagonist, for example labeled forskolin or a labeled forskolin analog. Varying concentrations of the candidate are supplied, along with a constant concentration of the labeled agonist or antagonist. The inhibition of binding of the labeled material can then be measured using established techniques. This measurement is then correlated to determine the amount and potency of the candidate that is bound to hAC5.

Another method of identifying compounds which affect hAC5 activity is the rational design of synthetic compounds based on nucleotide scaffolds, targeted to either of two distinct sites on the hAC5 enzyme. One of these is the active site (ATP being the substrate, cAMP being the product) and the other is the separate P site (adenine nucleoside 3'-polyphosphates reportedly demonstrating the greatest inhibitory activity, with either pure or crude enzyme preparations). As a related approach, one could attempt to design forskolin analogues which may demonstrate isoform specific effects.

In addition, using the above assays, the ability of a candidate drug to stimulate or inhibit the activity of hAC5 can be tested directly.

Once lead candidates are identified, and for purposes of demonstrating that isoform specificity may be achieved with small molecule modulators, it is desirable to develop assay systems which monitor most, and preferably all, human adenylyl cyclase isoforms. These assays may be used to evaluate either existing (e.g. forskolin analogs or P site inhibitors) or newly discovered small molecule modulators and determine structure activity relationships for different adenylyl cyclase isoforms. Such assays could also be used to evaluate either specific or selective modulators of other adenylyl targets and with use of a whole cell assay, may provide useful insights for designing bioavailability and addressing biological activity of lead candidates.

The hAC5 also has utility in assays for the diagnosis of diseases and disorders by detection, in tissue samples, of aberrant expression of the hAC5 enzyme.

Another aspect of the invention relates to hAC5 agonists that imitate the naturally occurring form of hAC5. These agonists are useful as control reagents in the above-mentioned assays to verify the workability of the assay system. In addition, agonists for hAC5 may exhibit useful effects in vivo in treating disease.

Another aspect of the invention relates to hAC5 antagonists that are modified forms of hAC5 peptides. Such antagonists bind to hAC5, and prevent enzyme-substrate interaction by blocking their binding to hAC5. Another group of compounds within the scope of the invention, are antagonists of hAC5 substrate, i.e., these are substrate inhibitors. Both these types of antagonists find utility in diminishing or mediating events based upon enzyme-substrate interaction such as cAMP production. Yet another second group of antagonists includes antibodies designed to bind specific portions of hAC5. In general, these are monoclonal antibody preparations which are highly specific for any desired region of hAC5, although polyclonal antibodies are also contemplated by this invention. The antibodies, which are explained in greater detail below, are also useful in immunoassays for the hAC5 enzyme, for example, in assessing successful expression of the gene in recombinant systems.

In both the agonists and antagonists, a preferred embodiment is that class of compounds having amino acid sequences that are encoded by the hAC5 gene. The invention also includes those compounds where one, two, three or more of said amino acid residues are replaced by one(s) which is not encoded genetically. Also included in the invention are isolated DNA molecules that encode these specific peptides.

It is believed that the extracellular domains of enzymes may play a key role in extracellular activities, for example, in enzyme regulation. Accordingly, the invention includes agonists and antagonists having amino acid sequences, in whole or in part, corresponding to the extracellular domains of hAC5, the sequences of which can be approximated from the amino acid sequence of FIG. 1 and the hydropathy analysis referred to in example 2. The invention also includes agonists and antagonists that affect the enzyme's function by binding to the N- or C-terminus or to one of the intracellular (ICD) domains of hAC5, the sequences of which can be approximated from the amino acid sequence of FIG. 1 and the hydropathy analysis.

In other adenylyl cyclases, the ICD IV and carboxy terminus regions have been shown to play a role in enzyme activity or $G_a$ or forskolin interaction. See for example: Whisnant, et al., supra. Accordingly, it is expected that the amino acid sequences of the ICD IV and carboxy terminus regions of hAC5, in whole or in part, will be particularly useful in designing antibodies or peptides that can bind the enzyme and block enzyme activity or $G_{as}$ interaction.

As the understanding of adenylyl cyclases and factors which effect isoform activity increases, rational drug design is becoming a viable alternative in pharmaceutical research. It is believed that the two conserved intracellular domains of adenylyl cyclase (the $C_1$ and $C_2$ domains) associate to form an active enzyme. This has been demonstrated with studies that combine both expressed recombinant $C_1$ and $C_2$ domains. Both the $C_1$ and $C_2$ domains are required to reconstitute enzyme activity while either alone has no substantial activity. Forskolin plus $G_{as}$ stimulates this system, by increasing the association of the two domains. Designing assays which monitor enzyme activity, dependent on association of two separate domains, is expected to provide greater sensitivity to antagonists since this would presumably be more easily disrupted. Other studies have demonstrated that peptides, comprised of sequences from conserved regions of the intracellular domains, act as inhibitors of detergent solubilized enzyme preparations. This invention contemplates the use of peptide walking strategies, to delimit regions of the modulator which may be responsible for its activity, leading to the design of small molecule inhibitors. Finally, knowledge of uncharacterized, physiological modulators of adenylyl cyclase, particularly those that demonstrate isoform specificity, may provide new assay systems for identifying novel AC modulators. It is expected that many of these modulators would be proteins and some may be identified while using adenylyl cyclase sequences as "bait" in a yeast two hybrid system. Alternatively one may identify proteins which coprecipitate with adenylyl cyclase upon capture with adenylyl cyclase antibodies.

The peptide agonists and antagonists of the invention are preferably about 10–100 amino acids in length, more preferably 25–75 amino acids in length. These peptides can be readily prepared using standard solid phase or solution phase peptide synthesis, as is well known in the art In addition, the DNA encoding these peptides can be synthesized using commercially available oligonucleotide synthesis instrumentation and recombinantly produced using standard recombinant production systems. Production using solid phase peptide synthesis is required when non-gene encoded amino acids are to be included in the peptide.

Another aspect of the invention pertains to antibodies, which have both diagnostic and therapeutic uses. Antibodies are able to act as antagonists or agonists by binding specific regions of the hAC5 polypeptide. These antibodies also find utility in immunoassays that measure the presence of hAC5, for example in immunoassays that measure gene expression. In general, antibodies to adenylyl cyclases, and more importantly, those which may recognize specific isoforms of adenylyl cyclase, are a useful tool to evaluate tissue distribution and prevalence of the adenylyl cyclase protein. By identifying regions of dissimilarity between the adenylyl cyclase isoforms and the antigenic potential of these regions, either synthetic peptides or recombinant proteins to these sequences can be created for use in immunization. The resulting antibodies would then be characterized for specificity based on the unique qualities of the immunogen and reactivity with other expressed isoforms. Detection of isoform protein in various tissues can readily be monitored by Westerns blots; however, immunohistochemical analysis would also be useful. This information is useful to identify the adenylyl cyclase target of interest, providing valuable insights into useful therapeutic strategies such as targets in cardiovascular disease, asthma or obesity.

The antibodies of the present invention can be prepared by techniques that are well known in the art. The antibodies can be monoclonal or polyclonal, but are preferably monoclonal antibodies that are highly specific for hAC5 and can be raised against the whole hAC5 polypeptide or regions thereof. Antibodies are prepared by immunizing suitable mammalian hosts (typically rabbit, rat, mouse, goat, human, etc.) in appropriate immunization protocols using the peptide haptens (immunogen) alone, if they are of sufficient length, or, if desired, or if required to enhance immunogenicity, conjugated to suitable carriers. The immunogen will typically contain a portion of the hAC5 polypeptide that is intended to be targeted by the antibodies. Critical regions include those regions corresponding to the extracellular domains of the hAC5 enzyme, any region(s) of proteolytic cleavage, and any segment(s) of the extracellular segment critical for activation. Methods for preparing immunogenic conjugates with carriers such as bovine serum albumin, keyhole limpet hemocyanin, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten can be extended at the amino or carboxy terminus with a cysteine residue or interspersed with cysteine residues, for example, to facilitate linking to carrier. The desired immunogen is administered to a host by injection over a suitable period of time using suitable adjuvants followed by collection of sera. Over the course of the immunization schedule, titers of antibodies are taken to determine the adequacy of antibody formation.

Polyclonal antibodies are suitable for many diagnostic and research purposes and are easily prepared. Monoclonal antibodies are often preferred for therapeutic applications and are prepared by continuous hybrid cell lines and collection of the secreted protein. Immortalized cell lines that secrete the desired monoclonal antibodies can be prepared by the method described in Kohler and Milstein, *Nature* 256:495–497 (1975) or modifications which effect immortalization of lymphocytes or spleen cells, as is generally known. The immortalized cell lines are then screened by immunoassay techniques in which the antigen is the immunogen or a cell expressing hAC5 on its surface. Cells that are found to secrete the desired antibody, can then be cultured in vitro or by production in the ascites fluid. The antibodies are then recovered from the culture supernatant or from the ascites supernatant.

Alternately, antibodies can be prepared by recombinant means, i.e., the cloning and expression of nucleotide sequences or mutagenized versions thereof that at a minimum code for the amino acid sequences required for specific binding of natural antibodies. Antibody regions that bind specifically to the desired regions of hAC5 can also be produced as chimeras with regions of multiple species origin.

Antibodies may include a complete immunoglobulin or a fragment thereof, and includes the various classes and isotypes such as IgA, IgD, IgE, IgG1, IgG2a, IgG2b, IgG3 and IgM. Fragments include Fab, Fv, F(ab')$_2$, Fab', and so forth. Fragments of the monoclonals or the polyclonal antisera which contain the immunologically significant portion can be used as antagonists, as well as the intact antibodies. Use of immunologically reactive fragments, such as the Fab, Fab', or F(ab')$_2$ fragments is often preferable, especially in a therapeutic context, as these fragments have different immunogenicity than the whole immunoglobulin, and do not carry the biological activity of an immunoglobulin constant domain.

The antibodies thus produced are useful not only as potential agonist or antagonists for the hAC5 polypeptide, filling the role of agonist or antagonist in the assays of the invention, but are also useful in immunoassays for detecting the hAC5 enzyme. As such these antibodies can be coupled to imaging agents for administration to a subject to allow detection of localized antibody to ascertain the under-or over-expression of hAC5 in tissues of interest. In addition, these reagents are useful in vitro to detect, for example, the successful production of hAC5 on the surface of the recombinant host cells.

Yet another aspect of the invention relates to pharmaceutical compositions containing the compounds and antibodies of the invention. The agonists and antagonists of the invention have therapeutic utility in (1) treating diseases caused by aberrant activity of the hAC5 enzyme in tissues where it is customarily found, for example in the heart and brain and (2) treating diseases whose symptoms can be ameliorated by stimulating or inhibiting the activity of hAC5.

The peptide agonists and antagonists of the invention can be administered in conventional formulations for systemic administration such as is well known in the art. Typical formulations may be found, for example, in *Remington's Pharmaeutical Sciences*, Mack Publishing Co., Easton Pa., latest edition.

Preferred forms of systemic administration include injection, typically by intravenous injection. Other injection routes, such as subcutaneous, intramuscular, or intraperitoneal, can also be used. More recently, alternative means for systemic administration of peptides have been devised which include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the patient's condition, and the judgment of the attending physician. Suitable dosage ranges, however, are in the range of 0.1–100 µg/kg of subject. Wide variations in the needed dosage, however, are to be expected in view of the variety of peptides available and the differing efficiencies of various routes of administration. For example, oral administration would be expected to require higher dosages than administration by intravenous injection. Variations in these dosage levels can be adjusted using standard empirical routines for optimization as is well understood in the art.

The invention also relates to the therapeutic, prophylactic and research uses of various techniques to block or modulate the expression of the hAC5 by interfering with the transcription of translation of a DNA or RNA molecule encoding the hAC5. This includes a method to inhibit or regulate expression of hAC5 in a cell comprising providing to the cell an oligonucleotide molecule which is antisense to, or forms a triple helix with, hAC5-encoding DNA or with DNA regulating expression of hAC5-encoding DNA, in an amount sufficient to inhibit or regulate expression of the hAC5, thereby inhibiting or regulating its expression. Also included is a method to inhibit or regulate expression of hAC5 in a subject, comprising administering to the subject an oligonucleotide molecule which is antisense to, or forms a triple helix with, hAC5-encoding DNA or with DNA regulating expression of hAC5-encoding DNA, in an amount sufficient to inhibit or regulate expression of hAC5 in the subject, thereby inhibiting or regulating its expression. The antisense molecule or triple helix-forming molecule in the above methods is preferably a DNA or RNA oligonucleotide. These utilities are described in greater detail below.

The constitutive expression of antisense RNA in cells has been shown to inhibit the expression of about 20 different genes in mammals and plants, and the list continually grows (Hambor, et al., *J. Exp. Med.* 168:1237–1245 (1988); Holt, et al., *Proc. Natl. Acad. Sci.* 83:4794–4798 (1986); Izant, et al., *Cell* 36:1007–1015 (1984); Izant, et al., *Science* 229:345–352 (1985) and De Benedetti, et al., *Proc. Natl. Acad. Sci.* 84:658–662 (1987)). Possible mechanisms for the antisense effect are the blockage of translation or prevention of splicing, both of which have been observed in vitro. Interference with splicing allows the use of intron sequences (Munroe, *EMBO. J.* 7:2523–2532 (1988) which should be less conserved and therefore result in greater specificity in inhibiting expression of a protein of one species but not its homologue in another species.

Therapeutic gene regulation is accomplished using the "antisense" approach, in which the function of a target gene in a cell or organism is blocked, by transfection of DNA, preferably an oligonucleotide, encoding antisense RNA which acts specifically to inhibit expression of the particular target gene. The sequence of the antisense DNA is designed to result in a full or preferably partial antisense RNA transcript which is substantially complementary to a segment of the gene or mRNA which it is intended to inhibit. The complementarity must be sufficient so that the antisense RNA can hybridize to the target gene (or mRNA) and inhibit the target gene's function, regardless of whether the action is at the level of splicing, transcription or translation. The degree of inhibition, readily discernible by one of ordinary skill in the art without undue experimentation, must be sufficient to inhibit, or render the cell incapable of expressing, the target gene. One of ordinary skill in the art will recognize that the antisense RNA approach is but one of a number of known mechanisms which can be employed to block specific gene expression.

By the term "antisense" is intended an RNA sequence, as well as a DNA sequence coding therefor, which is sufficiently complementary to a particular mRNA molecule for which the antisense RNA is specific to cause molecular hybridization between the antisense RNA and the mRNA such that translation of the mRNA is inhibited. Such hybridization must occur under in vivo conditions, that is, inside the cell. The action of the antisense RNA results in specific inhibition of gene expression in the cell. See Albers, et al., "Molecular Biology Of The Cell", 2nd Ed., Garland Publishing, Inc., New York, N.Y. (1989), in particular, pages 195–196.

The antisense RNA of the present invention may be hybridizable to any of several portions of a target mRNA, including the coding sequence, a 3' or 5' untranslated region, or other intronic sequences. A preferred antisense RNA is that complementary to hAC5 mRNA. As is readily discernible by one of skill in the art, the minimal amount of homology required by the present invention is that sufficient to result in hybridization to the specific target mRNA and inhibition of its translation or function while not affecting function of other mRNA molecules and the expression of other genes.

Antisense RNA is delivered to a cell by transformation or transfection with a vector into which has been placed DNA encoding the antisense RNA with the appropriate regulatory sequences, including a promoter, to result in expression of the antisense RNA in a host cell.

"Triple helix" or "triplex" approaches involve production of synthetic oligonucleotides which bind to the major groove of a duplex DNA to form a colinear triplex. Such triplex formation can regulate and inhibit cellular growth. See, for example, Hogan, et al., U.S. Pat. No. 5,176,996; Cohen, et al., *Sci Amer.*, December 1994, p. 76–82; Helene, *Anticanecr Drug Design* 6:569–584 (1991); Maher III, et al., *Antisense Res. Devel.* 1:227–281 (Fall 1991); and Crook, et al. eds., "Antisense Research and Applications", CRC Press, 1993; all of which are incorporated herein by reference. It is based in part on the discovery that a DNA oligonucleotide can bind by triplex formation to a duplex DNA target in a gene regulatory region, thereby repressing transcription initiation (Cooney, et. al. *Science* 241:456 (1988)). The present invention utilizes methods such as those of Hogan et al., supra, to designing oligonucleotides which will bind tightly and specifically to a duplex DNA target comprising part of the hAC5-encoding DNA or a regulatory sequence thereof. Such triplex oligonucleotides can therefore be used as a class of drug molecules to selectively manipulate the expression of this gene.

Thus the present invention is directed to providing to a cell or administering to a subject a synthetic oligonucleotide in sufficient quantity for cellular uptake and binding to a DNA duplex of the target hAC5-coding DNA sequence or a regulatory sequence thereof, such that the oligonucleotide binds to the DNA duplex to form a colinear triplex. This method is used to inhibit expression of the hAC5 enzyme on cells in vitro or in vivo. Preferably the target sequence is positioned within the DNA domain adjacent to the RNA transcription origin. This method can also be used to inhibit growth of cells which is dependent on expression of this enzyme. The method may also be used to alter the relative amounts or proportions of the hAC5 expressed on cells or tissues by administering such a triplex-forming synthetic oligonucleotide.

The following examples are intended to illustrate but not to limit the invention.

EXAMPLE 1

Construction and Screening of a Human Heart cDNA Library

Whole human heart was used as a source of mRNA. The libraries were purchased from a commercial source, Clontech (Catalog No. HL3026a). The libraries were prepared in a lambda gt10 phage with both oligo-dT and random primers. The primary screening of the lambda gt10 library was carried out with gentle washing (less stringent conditions). Prehybridization and hybridization were carried out at standard conditions. A suitable PCR AC fragment was used as a probe.

The probe was radiolabeled with $^{32}$P-dCTP by the random primer labeling method. After hybridization, the blot was washed under increasingly stringent conditions and then radioautographed. A positive clone was obtained.

The next step was to ascertain the fill length cDNA sequence from the inserts in the clones. All the positive clones from the human heart library were subcloned into a suitable plasmid. After restriction maps were made, they were further subcloned and sequenced with universal primers or synthesized oligomers. The sequence was performed bidirectionally with Sequenase (Tabor, et al., *Proc. Natl. Acad. Sci. USA* 84:4767–4771 (1987).

Clone were either used on their own, or sequenced and then used to generate PCR primers which were used to acquire additional clones of interest, by the PCR-based RACE ("rapid amplification of cDNA ends") technique (Frohman, M. A., *Methods Enzymol.* 218:340–362 (1991)) and human heart mRNA. One clone of particular interest was used as a probe to screen a separate human heart library and several more clones were obtained. Sequencing revealed an open reading frame of 3783 bases reads through to a TGA, a translation termination codon (FIG. 1). Thus, the clone(s) encode a protein of 1261 amino acids. The entire coding portion of the cDNA and its deduced amino acid sequence are shown (FIG. 1) (SEQ ID NO: 1 and 2, respectively).

One or more fragments from these clones were subcloned into pcDNA3, obtained from Invitrogen. The resulting expression vector, containing the full length cDNA, was given a designation. Samples of this expression vector, inserted into an appropriate *E. coli* strain were deposited with the American Type Culture Collection, in Manassas, Va., on Mar. 5, 2002 in accordance with the Budapest Treaty on the International Recognition of the Deposit of Microorganisms for the Purposes of Patent Procedure and have been accorded Patent Depository No. PTA-4115.

EXAMPLE 2

Cloning a Expression of the Human Type V Adenylyl Cyclase

The human type V adenylyl cyclase was produced by cloning and expressing heart type V adenylyl cyclase cDNA in a suitable expression system using recombinant DNA methods, such as are well known in the art.

Purified plasmid was transfected into HEK-293 cells using electroporation. The cells were grown in an appropriate growth medium then washed. After the addition of trypsin solution, the cells were incubated, harvested and resuspended in the growth media. Purified plasmid was added to an electroporation cuvette. Cells were added to the DNA and the mixture was pulsed. The cell-DNA mixture was then plated into a suitable growth media. The plate was incubated before placing cells on a suitable selective media.

phAC5, having 1261 amino acids, was analyzed for secondary structure by the method of Kyte, et al., *J. Mol. Biol.* 157:105–132 (1982). The software, GeneWorks; v.2.45; IntelliGenetics, Inc.; Mountain View; Calif. was used to obtain a hydropathy plot, and thereby identify the membrane related structure of this adenylyl cyclase isoform. The method of Kyte, et al., supra, was used with a window size of 5.

Thirteen peaks appear in the hydropathy plot, not shown, which represent transmembrane spanning regions. Peaks 1–12 represent transmembrane spanning regions. These results suggest that this adenylyl cyclase isoform has a structure of twelve transmembrane spanning regions, as well as a large cytoplasmic loop located in the middle and at the end, which is consistent with the structures of the previously characterized isoforms. In the transmembrane positions, the fifth extracellular loop is the largest (between the ninth and tenth transmembrane spans). The peak designated "–1" corresponds to the N-terminus region. In all other isoforms, the N-terminus is intracellular. The appearance of peak "–1" on the hydropathy plot raises the possibility that the N-terminus of this isoform is extracellular.

EXAMPLE 3

Evaluation of the Human Type V Adenylyl Cyclase

The biochemical characteristics of hAC9 were determined in a stable expression system using HEK-293 cells. A fragment of the adenylyl cyclase cDNA containing the whole coding sequence was inserted into a suitable plasmid.

An assay was performed to measure cAMP product formation and it was determined that the hAC5 enzyme expressed by this cDNA was active.

EXAMPLE 4

Tissue Distribution of the Human Type V Adenylyl Cyclase

In order to determine the tissue distribution of hAC5, Northern blotting was performed using mRNA from various tissues. Messenger RNA was purified using guanidium sodium and oligo-dT columns from various human tissues.

The blot was pre-hybridized in a suitable solution before the addition of a probe. Hybridization was performed, followed by washing under increasingly stringent conditions. The blot was then autoradiographed.

The results of the Northern blot analysis indicated that hAC5 is predominantly expressed in heart and brain tissue. The brain shows somewhat less expression that in the heart.

All references cited and mentioned above, including patents, journal articles and texts, are all incorporated by reference herein, whether expressly incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An isolated nucleic acid molecule encoding a type V adenylyl cyclase comprising SEQ ID NO: 2, or the complement thereof.

2. The isolated nucleic acid molecule of claim 1, wherein the nucleic acid molecule comprises nucleotides 139–3921 of SEQ ID NO: 1.

3. The isolated nucleic acid molecule of claim 1, wherein the nucleic acid molecule consists of nucleotides 139–3921 of SEQ ID NO: 1.

4. The isolated nucleic acid molecule of claim 1, wherein the nucleic acid molecule comprises nucleotides 139–3924 of SEQ ID NO: 1.

5. An isolated nucleic acid molecule of claim 1, wherein the adenylyl cyclase comprises SEQ ID NO: 2.

6. An isolated nucleic acid molecule encoding a soluble fragment of SEQ ID NO: 2 having type V adenylyl cyclase activity.

7. The isolated nucleic acid molecule of any one of claims 1–6, wherein said nucleic acid molecule is operably linked to one or more expression control elements.

8. A vector comprising an isolated nucleic acid molecule of any one of claims 1–6.

9. A host cell transformed to contain the nucleic acid molecule of any one of claims 1–6.

10. A host cell comprising the vector of claim 8.

11. The host cell of claim 10, wherein said host is selected from the group consisting of prokaryotic host cells and eukaryotic host cells.

12. The host cell of claim 10, wherein said host cell is a virally transformed human cell line.

13. The host cell of claim 10, wherein said host cell is an HEK-293 cell line.

14. A method of expressing a human type V adenylyl cyclase protein, comprising: culturing a transformed host cell of claim 10 under conditions which result in expression of the human type V adenylyl cyclase protein.

* * * * *

SEQUENCE LISTING

<160> NUMBER OF SEQ ID NOS: 2

<210> SEQ ID NO 1
<211> LENGTH: 4523
<212> TYPE: DNA
<213> ORGANISM: human type V adenylyl cyclase
<220> FEATURE:
<221> NAME/KEY: CDS
<222> LOCATION: (139)..(3921)

<400> SEQUENCE: 1

```
gctgcagcgc agggccccgg gccgccccg acgtgtgacc ctagcctggt cccctgctc        60 ggccgtccgc cctcccttg gagaccccg gcccggcttc cggggagga ggaaggagac        120 gacgaggccg aggggggg atg tcc ggc tcc aaa agc gtg agc ccc ccg ggc       171
                    Met Ser Gly Ser Lys Ser Val Ser Pro Pro Gly
                     1               5                      10 tac gcg gcg cag aag act gcg gcg ccg gcg ccc cgg gga ggc ccc gaa       219
Tyr Ala Ala Gln Lys Thr Ala Ala Pro Ala Pro Arg Gly Gly Pro Glu
                15                  20                  25 cac cgc tct gcg tgg ggc gag gcc gat tcc cgc gcg aat ggc tac ccc       267
His Arg Ser Ala Trp Gly Glu Ala Asp Ser Arg Ala Asn Gly Tyr Pro
        30                  35                  40 cat gcc ccc ggg ggt tct gcc cgc ggc tcc acc aag aaa ccc ggg ggg       315
His Ala Pro Gly Gly Ser Ala Arg Gly Ser Thr Lys Lys Pro Gly Gly
    45                  50                  55 gcg gtg acc ccg cag cag cag cgc ctg gcc agc cgc tgg cgc agc           363
Ala Val Thr Pro Gln Gln Gln Arg Leu Ala Ser Arg Trp Arg Ser
60                  65                  70                  75 gac gac gac gac gat cct ccg ctg agc ggt gac gac ccc ctg gcc ggg       411
Asp Asp Asp Asp Asp Pro Pro Leu Ser Gly Asp Asp Pro Leu Ala Gly
                80                  85                  90 ggc ttc ggc ttc agc ttc cgc tcc aag tcc gcc tgg cag gag cgc ggc       459
Gly Phe Gly Phe Ser Phe Arg Ser Lys Ser Ala Trp Gln Glu Arg Gly
                95                  100                 105 ggc gac gac tgc ggt cgc ggc agc cgc cgg cag cgg cgg ggc gcg gcc       507
Gly Asp Asp Cys Gly Arg Gly Ser Arg Arg Gln Arg Arg Gly Ala Ala
            110                 115                 120 agc ggg ggc agc acc cgg gcg ccc cct gcg ggc ggc ggc ggc tcg           555
Ser Gly Gly Ser Thr Arg Ala Pro Pro Ala Gly Gly Gly Gly Ser
125                 130                 135 gcg gcg gcg gct gcc tcg gcg ggc ggg acg gag gtg cgc cct cgc tcg       603
Ala Ala Ala Ala Ala Ser Ala Gly Gly Thr Glu Val Arg Pro Arg Ser
140                 145                 150                 155 gtg gag gtg ggt ctg gag gag cgg cgg ggc aag ggg cgc gcg gcc gac       651
Val Glu Val Gly Leu Glu Glu Arg Arg Gly Lys Gly Arg Ala Ala Asp
                160                 165                 170 gag ctg gag gcc ggc gcc gtc gag ggc ggc gag ggg tcc ggg gat ggc       699
Glu Leu Glu Ala Gly Ala Val Glu Gly Gly Glu Gly Ser Gly Asp Gly
            175                 180                 185 ggc agc tcg gcg gac tcg ggc tcg ggc gcg ggg ccc ggc gcg gtg ctg       747
Gly Ser Ser Ala Asp Ser Gly Ser Gly Ala Gly Pro Gly Ala Val Leu
        190                 195                 200 tcc ctg ggc gcc tgc tgc ctg gcg ttg ctg cag ata ttc cgc tcc aag       795
Ser Leu Gly Ala Cys Cys Leu Ala Leu Leu Gln Ile Phe Arg Ser Lys
    205                 210                 215 aag ttc ccg tcg gac aaa ctg gag cgg ctg tac cag cgc tac ttc ttc       843
Lys Phe Pro Ser Asp Lys Leu Glu Arg Leu Tyr Gln Arg Tyr Phe Phe
220                 225                 230                 235
```

```
cgc ctg aac cag agc agc ctc acc atg ctc atg gcc gtg ctg gtg ctc      891
Arg Leu Asn Gln Ser Ser Leu Thr Met Leu Met Ala Val Leu Val Leu
            240                 245                 250 gtg tgc ctg gtc atg ttg gcc ttc cac gcg gcg cgg ccc ccg ctc cag      939
Val Cys Leu Val Met Leu Ala Phe His Ala Ala Arg Pro Pro Leu Gln
            255                 260                 265 ctg ccc tac ctg gcc gtg ctg gcg gcc gcc gtc ggc gtg atc ctc atc      987
Leu Pro Tyr Leu Ala Val Leu Ala Ala Ala Val Gly Val Ile Leu Ile
            270                 275                 280 atg gct gtg ctt tgc aac cgc gcc gcc ttc cac cag gac cac atg ggc     1035
Met Ala Val Leu Cys Asn Arg Ala Ala Phe His Gln Asp His Met Gly
        285                 290                 295 ctg gcc tgc tat gcg ctc atc gcc gtg gtg ctg gcc gtc cag gtg gtg     1083
Leu Ala Cys Tyr Ala Leu Ile Ala Val Val Leu Ala Val Gln Val Val
300                 305                 310                 315 ggc ctg ctg ctg ccg cag cca cgc agc gcc tct gag ggc atc tgg tgg     1131
Gly Leu Leu Leu Pro Gln Pro Arg Ser Ala Ser Glu Gly Ile Trp Trp
            320                 325                 330 acc gtg ttc ttc atc tac acc atc tac acg ctg ctg ccc gtg cgc atg     1179
Thr Val Phe Phe Ile Tyr Thr Ile Tyr Thr Leu Leu Pro Val Arg Met
            335                 340                 345 cgg gcc gca gtg ctc agc ggg gtg ctc ctg tcc gcc ctc cac ctg gcc     1227
Arg Ala Ala Val Leu Ser Gly Val Leu Leu Ser Ala Leu His Leu Ala
            350                 355                 360 atc gcc ctg cgc acc aac gcc cag gac cag ttc ctg ctg aag cag ctt     1275
Ile Ala Leu Arg Thr Asn Ala Gln Asp Gln Phe Leu Leu Lys Gln Leu
        365                 370                 375 gtc tcc aat gtt ctc att ttc tcc tgc acc aac atc gtg ggt gtc tgc     1323
Val Ser Asn Val Leu Ile Phe Ser Cys Thr Asn Ile Val Gly Val Cys
380                 385                 390                 395 acc cac tat ccg gct gag gtc tcc cag aga cag gct ttc cag gag acc     1371
Thr His Tyr Pro Ala Glu Val Ser Gln Arg Gln Ala Phe Gln Glu Thr
                400                 405                 410 cga gag tgc atc cag gcg cgg ctc cac tcg cag cgg gag aac cag cag     1419
Arg Glu Cys Ile Gln Ala Arg Leu His Ser Gln Arg Glu Asn Gln Gln
            415                 420                 425 cag gaa cgg ctc ctg ctg tct gtc ctt ccc cgt cat gtt gcc atg gag     1467
Gln Glu Arg Leu Leu Leu Ser Val Leu Pro Arg His Val Ala Met Glu
            430                 435                 440 atg aaa gca gac atc aac gcc aag cag gag gat atg atg ttc cat aag     1515
Met Lys Ala Asp Ile Asn Ala Lys Gln Glu Asp Met Met Phe His Lys
        445                 450                 455 att tac atc cag aaa cat gac aac gtg agc atc ctg ttt gct gac atc     1563
Ile Tyr Ile Gln Lys His Asp Asn Val Ser Ile Leu Phe Ala Asp Ile
460                 465                 470                 475 gag ggc ttc acc agc ctg gcg tcc cag tgc act gca cag gaa ctg gtc     1611
Glu Gly Phe Thr Ser Leu Ala Ser Gln Cys Thr Ala Gln Glu Leu Val
                480                 485                 490 atg acc ctc aac gag ctc ttc gcc cgc ttt gac aag ctg gcc gca gag     1659
Met Thr Leu Asn Glu Leu Phe Ala Arg Phe Asp Lys Leu Ala Ala Glu
            495                 500                 505 aat cac tgt tta cgt att aag atc ctt ggg gat tgt tat tac tgc gtc     1707
Asn His Cys Leu Arg Ile Lys Ile Leu Gly Asp Cys Tyr Tyr Cys Val
            510                 515                 520 tcg ggg ctg cct gaa gca agg gct gac cac gcc cac tgc tgt gtg gag     1755
Ser Gly Leu Pro Glu Ala Arg Ala Asp His Ala His Cys Cys Val Glu
        525                 530                 535 atg ggc atg gac atg atc gag gcc atc tcg ttg gtc cgg gag gtg aca     1803
Met Gly Met Asp Met Ile Glu Ala Ile Ser Leu Val Arg Glu Val Thr
540                 545                 550                 555
```

```
ggg gtg aac gtg aac atg cgt gtg gga att cac agc ggg cga gta cac    1851
Gly Val Asn Val Asn Met Arg Val Gly Ile His Ser Gly Arg Val His
                560                 565                 570 tgc ggt gtc ctt ggt ctc agg aag tgg cag ttc gac gtc tgg tct aac    1899
Cys Gly Val Leu Gly Leu Arg Lys Trp Gln Phe Asp Val Trp Ser Asn
                575                 580                 585 gat gtc acg cta gcc aac cac atg gag gct ggc ggc aag gca gga cgc    1947
Asp Val Thr Leu Ala Asn His Met Glu Ala Gly Gly Lys Ala Gly Arg
                590                 595                 600 atc cac atc acc aag gct aca ctc aac tac ctg aat ggg gac tac gag    1995
Ile His Ile Thr Lys Ala Thr Leu Asn Tyr Leu Asn Gly Asp Tyr Glu
                605                 610                 615 gtg gag cca ggc tgt ggg ggc gag cgc aac gcc tac ctc aag gag cac    2043
Val Glu Pro Gly Cys Gly Gly Glu Arg Asn Ala Tyr Leu Lys Glu His
                620                 625                 630                 635 agt atc gag acc ttc ctc atc ctg cgc tgc acc cag aag cgg aaa gaa    2091
Ser Ile Glu Thr Phe Leu Ile Leu Arg Cys Thr Gln Lys Arg Lys Glu
                        640                 645                 650 gag aag gcc atg atc gcc aag atg aac cgc cag aga acc aac tcc atc    2139
Glu Lys Ala Met Ile Ala Lys Met Asn Arg Gln Arg Thr Asn Ser Ile
                655                 660                 665 ggg cac aac cca cca cac tgg ggg gct gag cgc ccc ttc tac aac cac    2187
Gly His Asn Pro Pro His Trp Gly Ala Glu Arg Pro Phe Tyr Asn His
                670                 675                 680 ctg ggt ggc aac cag gtg tcc aag gag atg aag cgg atg ggc ttt gaa    2235
Leu Gly Gly Asn Gln Val Ser Lys Glu Met Lys Arg Met Gly Phe Glu
                685                 690                 695 gac ccc aag gac aag aac gcc cag gag agt gcg aac cct gag gat gaa    2283
Asp Pro Lys Asp Lys Asn Ala Gln Glu Ser Ala Asn Pro Glu Asp Glu
700                 705                 710                 715 gtg gat gag ttt ctg ggc cgt gcc att gac gcc agg agc att gat agg    2331
Val Asp Glu Phe Leu Gly Arg Ala Ile Asp Ala Arg Ser Ile Asp Arg
                        720                 725                 730 ctt cgg tct gag cac gtc cgc aag ttc ctc ctg acc ttc agg gag cct    2379
Leu Arg Ser Glu His Val Arg Lys Phe Leu Leu Thr Phe Arg Glu Pro
                735                 740                 745 gac tta gag aag aag tac tcc aag cag gta gac gac cga ttt ggt gcc    2427
Asp Leu Glu Lys Lys Tyr Ser Lys Gln Val Asp Asp Arg Phe Gly Ala
                750                 755                 760 tat gtg gcg tgt gcc tcg ctc gtc ttc ctc ttc atc tgc ttt gtc cag    2475
Tyr Val Ala Cys Ala Ser Leu Val Phe Leu Phe Ile Cys Phe Val Gln
                765                 770                 775 atc acc atc gtg ccc cac tcc ata ttc atg ctc agc ttc tac ctg acc    2523
Ile Thr Ile Val Pro His Ser Ile Phe Met Leu Ser Phe Tyr Leu Thr
780                 785                 790                 795 tgt tcc ctg ctg ctg acc ttg gtg gtg ttt gtg tct gtg atc tac tcc    2571
Cys Ser Leu Leu Leu Thr Leu Val Val Phe Val Ser Val Ile Tyr Ser
                        800                 805                 810 tgc gta aag ctc ttc ccc tcc cca ctg cag acc ctc tcc agg aag atc    2619
Cys Val Lys Leu Phe Pro Ser Pro Leu Gln Thr Leu Ser Arg Lys Ile
                815                 820                 825 gtg cgg tcc aag atg aac agc acc ctg gtt ggg gtg ttc acc atc acc    2667
Val Arg Ser Lys Met Asn Ser Thr Leu Val Gly Val Phe Thr Ile Thr
                830                 835                 840 ctg gtg ttc ctg gcg gct ttt gtc aac atg ttc acg tgc aac tcc agg    2715
Leu Val Phe Leu Ala Ala Phe Val Asn Met Phe Thr Cys Asn Ser Arg
                845                 850                 855 gac ctg ctg ggc tgc ttg gca cag gag cac aac atc agc gcg agc cag    2763
Asp Leu Leu Gly Cys Leu Ala Gln Glu His Asn Ile Ser Ala Ser Gln
```

```
                                          -continued 860               865                870              875 gtc aac gcg tgt cac gtg gcg gag tcg gcc gtc aac tac agc ctg ggc       2811
Val Asn Ala Cys His Val Ala Glu Ser Ala Val Asn Tyr Ser Leu Gly
            880                 885                 890 gat gag cag ggc ttc tgt ggc agc ccc tgg ccc aac tgc aac ttc ccc       2859
Asp Glu Gln Gly Phe Cys Gly Ser Pro Trp Pro Asn Cys Asn Phe Pro
        895                 900                 905 gag tac ttc acc tac agc gtg ctg ctc agc ctg ctg gcc tgc tcc gtg       2907
Glu Tyr Phe Thr Tyr Ser Val Leu Leu Ser Leu Leu Ala Cys Ser Val
    910                 915                 920 ttc ctg cag atc agc tgc atc ggg aag ctg gtg ctc atg ctg gcc atc       2955
Phe Leu Gln Ile Ser Cys Ile Gly Lys Leu Val Leu Met Leu Ala Ile
925                 930                 935 gag ctc atc tac gtg ctc atc gtg gag gtg cca ggt gtc acg ctc ttc       3003
Glu Leu Ile Tyr Val Leu Ile Val Glu Val Pro Gly Val Thr Leu Phe
940                 945                 950                 955 gac aac gcc gac ctg ctg gtc acc gcc aac gcc ata gac ttc ttc aac       3051
Asp Asn Ala Asp Leu Leu Val Thr Ala Asn Ala Ile Asp Phe Phe Asn
            960                 965                 970 aac ggg acc tcc cag tgc cct gag cat gca acc aag gtg gca ttg aag       3099
Asn Gly Thr Ser Gln Cys Pro Glu His Ala Thr Lys Val Ala Leu Lys
        975                 980                 985 gtg gtg acg ccc atc atc atc tca gtc ttt gtg ctg gcc ctg tac ctg       3147
Val Val Thr Pro Ile Ile Ile Ser Val Phe Val Leu Ala Leu Tyr Leu
    990                 995                 1000 cac gcc cag cag gtg gag tcc act gcc cgc ctc gac ttc ctc tgg aaa       3195
His Ala Gln Gln Val Glu Ser Thr Ala Arg Leu Asp Phe Leu Trp Lys
1005                1010                1015 ctg cag gcc aca gag gag aaa gag gag atg gag gag ctg cag gcc tac       3243
Leu Gln Ala Thr Glu Glu Lys Glu Glu Met Glu Glu Leu Gln Ala Tyr
1020                1025                1030                1035 aac cgg cgg ctg ctg cac aac atc ctg ccc aag gac gtg gcc gct cac       3291
Asn Arg Arg Leu Leu His Asn Ile Leu Pro Lys Asp Val Ala Ala His
            1040                1045                1050 ttc ctg gcc cgc gag cgg cgc aat gat gag ctc tac tat cag tcc tgt       3339
Phe Leu Ala Arg Glu Arg Arg Asn Asp Glu Leu Tyr Tyr Gln Ser Cys
        1055                1060                1065 gag tgt gtg gcg gtc atg ttc gcc tcc atc gcc aac ttc tcc gag ttc       3387
Glu Cys Val Ala Val Met Phe Ala Ser Ile Ala Asn Phe Ser Glu Phe
    1070                1075                1080 tac gtt gag ctg gag gcc aac aac gag ggt gtc gag tgc ctg cgg cta       3435
Tyr Val Glu Leu Glu Ala Asn Asn Glu Gly Val Glu Cys Leu Arg Leu
1085                1090                1095 ctc aat gag atc atc gct gac ttt gat gag atc atc agc gag gat cgg       3483
Leu Asn Glu Ile Ile Ala Asp Phe Asp Glu Ile Ile Ser Glu Asp Arg
1100                1105                1110                1115 ttc cgg cag ctg gag aag atc aag acc atc ggc agc acc tac atg gct       3531
Phe Arg Gln Leu Glu Lys Ile Lys Thr Ile Gly Ser Thr Tyr Met Ala
            1120                1125                1130 gcc tcc ggc ctc aac gac tct acc tac gac aag gtg ggc aag acc cac       3579
Ala Ser Gly Leu Asn Asp Ser Thr Tyr Asp Lys Val Gly Lys Thr His
        1135                1140                1145 atc aag gca ctg gcc gac ttt gcc atg aag ctg atg gac cag atg aag       3627
Ile Lys Ala Leu Ala Asp Phe Ala Met Lys Leu Met Asp Gln Met Lys
    1150                1155                1160 tac atc aat gag cac tcc ttc aac aac ttc cag atg aag atc ggg ctc       3675
Tyr Ile Asn Glu His Ser Phe Asn Asn Phe Gln Met Lys Ile Gly Leu
1165                1170                1175 aac atc ggc ccc gtg gtg gcc ggg gtg ata ggg gca cga aag cct cag       3723
```

-continued

```
Asn Ile Gly Pro Val Val Ala Gly Val Ile Gly Ala Arg Lys Pro Gln
    1180                1185                1190                1195 tac gac atc tgg ggc aat acc gtg aac gtg gcc agc cgc atg gac agc    3771
Tyr Asp Ile Trp Gly Asn Thr Val Asn Val Ala Ser Arg Met Asp Ser
            1200                1205                1210 acc ggt gta ccc gac cgc atc cag gtc acc aca gac atg tac cag gtg    3819
Thr Gly Val Pro Asp Arg Ile Gln Val Thr Thr Asp Met Tyr Gln Val
        1215                1220                1225 ctg gct gcc aac acg tac cag ctg gag tgc cgg ggc gtg gtc aag gtc    3867
Leu Ala Ala Asn Thr Tyr Gln Leu Glu Cys Arg Gly Val Val Lys Val
        1230                1235                1240 aag ggc aaa ggc gag atg atg acc tac ttc ctc aat gga ggg ccc ccg    3915
Lys Gly Lys Gly Glu Met Met Thr Tyr Phe Leu Asn Gly Gly Pro Pro
    1245                1250                1255 ctc agt tagcagctgt tggccaatgg tgccaggcag cctggcctcc agaggcatgg    3971
Leu Ser
1260 aagcagcttc tctgtgtgcc gggggtggcg gggaagccat gctccagccc gcagggctgc    4031 gctgctgaga ttttccactt ggactccaga gcagcttctg cctttgctgg tgggcagcgg    4091 cctctgtccc aggccccggg gtgccagcgt cctgcgagca cccagctgac caaagatgtt    4151 tccctctgta gaagactctg ctagactggg tctgaagctt gagttttcta acaggtgctg    4211 ctgcacaggt ggaaaggagc cgtgggaatg tgtgtgtggc acggcccaga caagggcagg    4271 gctgaggggc ctccgactca gctgggggta cgggctcg aatgtggcct gggagagcct    4331 agggggcccc agggtctgc ttttctatgt gagcctttaa acttcagaca ggccaccacc    4391 ctgcacctgc aggggctttg gcacaggagt gctggctttg gagggactgt ggccttcatc    4451 gtggtcctct gcccacacct ccacgcacac agacagtgcc ctaggaggga aacagaacta    4511 attacgaggg gg                                                         4523
```

<210> SEQ ID NO 2
<211> LENGTH: 1261
<212> TYPE: PRT
<213> ORGANISM: human type V adenylyl cyclase

<400> SEQUENCE: 2

```
Met Ser Gly Ser Lys Ser Val Ser Pro Gly Tyr Ala Ala Gln Lys
  1               5                  10                  15

Thr Ala Ala Pro Ala Pro Arg Gly Gly Pro Glu His Arg Ser Ala Trp
            20                  25                  30

Gly Glu Ala Asp Ser Arg Ala Asn Gly Tyr Pro His Ala Pro Gly Gly
        35                  40                  45

Ser Ala Arg Gly Ser Thr Lys Lys Pro Gly Gly Ala Val Thr Pro Gln
    50                  55                  60

Gln Gln Gln Arg Leu Ala Ser Arg Trp Arg Ser Asp Asp Asp Asp
65                  70                  75                  80

Pro Pro Leu Ser Gly Asp Asp Pro Leu Ala Gly Gly Phe Gly Phe Ser
                85                  90                  95

Phe Arg Ser Lys Ser Ala Trp Gln Glu Arg Gly Gly Asp Asp Cys Gly
            100                 105                 110

Arg Gly Ser Arg Arg Gln Arg Arg Gly Ala Ala Ser Gly Gly Ser Thr
        115                 120                 125

Arg Ala Pro Pro Ala Gly Gly Gly Gly Ser Ala Ala Ala Ala
    130                 135                 140

Ser Ala Gly Gly Thr Glu Val Arg Pro Arg Ser Val Glu Val Gly Leu
```

```
145                 150                 155                 160
Glu Glu Arg Arg Gly Lys Gly Arg Ala Ala Asp Glu Leu Glu Ala Gly
                165                 170                 175
Ala Val Glu Gly Gly Glu Gly Ser Gly Asp Gly Ser Ser Ala Asp
                180                 185                 190
Ser Gly Ser Gly Ala Gly Pro Gly Ala Val Leu Ser Leu Gly Ala Cys
            195                 200                 205
Cys Leu Ala Leu Leu Gln Ile Phe Arg Ser Lys Lys Phe Pro Ser Asp
        210                 215                 220
Lys Leu Glu Arg Leu Tyr Gln Arg Tyr Phe Arg Leu Asn Gln Ser
225                 230                 235                 240
Ser Leu Thr Met Leu Met Ala Val Leu Val Cys Leu Val Met
                245                 250                 255
Leu Ala Phe His Ala Ala Arg Pro Pro Leu Gln Leu Pro Tyr Leu Ala
            260                 265                 270
Val Leu Ala Ala Ala Val Gly Val Ile Leu Ile Met Ala Val Leu Cys
        275                 280                 285
Asn Arg Ala Ala Phe His Gln Asp His Met Gly Leu Ala Cys Tyr Ala
    290                 295                 300
Leu Ile Ala Val Val Leu Ala Val Gln Val Val Gly Leu Leu Leu Pro
305                 310                 315                 320
Gln Pro Arg Ser Ala Ser Glu Gly Ile Trp Trp Thr Val Phe Phe Ile
                325                 330                 335
Tyr Thr Ile Tyr Thr Leu Leu Pro Val Arg Met Arg Ala Ala Val Leu
                340                 345                 350
Ser Gly Val Leu Leu Ser Ala Leu His Leu Ala Ile Ala Leu Arg Thr
            355                 360                 365
Asn Ala Gln Asp Gln Phe Leu Leu Lys Gln Leu Val Ser Asn Val Leu
    370                 375                 380
Ile Phe Ser Cys Thr Asn Ile Val Gly Val Cys Thr His Tyr Pro Ala
385                 390                 395                 400
Glu Val Ser Gln Arg Gln Ala Phe Gln Glu Thr Arg Glu Cys Ile Gln
                405                 410                 415
Ala Arg Leu His Ser Gln Arg Glu Asn Gln Gln Gln Glu Arg Leu Leu
            420                 425                 430
Leu Ser Val Leu Pro Arg His Val Ala Met Glu Met Lys Ala Asp Ile
        435                 440                 445
Asn Ala Lys Gln Glu Asp Met Met Phe His Lys Ile Tyr Ile Gln Lys
    450                 455                 460
His Asp Asn Val Ser Ile Leu Phe Ala Asp Ile Glu Gly Phe Thr Ser
465                 470                 475                 480
Leu Ala Ser Gln Cys Thr Ala Gln Glu Leu Val Met Thr Leu Asn Glu
            485                 490                 495
Leu Phe Ala Arg Phe Asp Lys Leu Ala Ala Glu Asn His Cys Leu Arg
        500                 505                 510
Ile Lys Ile Leu Gly Asp Cys Tyr Tyr Cys Val Ser Gly Leu Pro Glu
    515                 520                 525
Ala Arg Ala Asp His Ala His Cys Cys Val Glu Met Gly Met Asp Met
    530                 535                 540
Ile Glu Ala Ile Ser Leu Val Arg Glu Val Thr Gly Val Asn Val Asn
545                 550                 555                 560
Met Arg Val Gly Ile His Ser Gly Arg Val His Cys Gly Val Leu Gly
                565                 570                 575
```

-continued

```
Leu Arg Lys Trp Gln Phe Asp Val Trp Ser Asn Asp Val Thr Leu Ala
            580                 585                 590
Asn His Met Glu Ala Gly Gly Lys Ala Gly Arg Ile His Ile Thr Lys
            595                 600                 605
Ala Thr Leu Asn Tyr Leu Asn Gly Asp Tyr Glu Val Glu Pro Gly Cys
            610                 615                 620
Gly Gly Glu Arg Asn Ala Tyr Leu Lys Glu His Ser Ile Glu Thr Phe
625                 630                 635                 640
Leu Ile Leu Arg Cys Thr Gln Lys Arg Lys Glu Lys Ala Met Ile
                    645                 650                 655
Ala Lys Met Asn Arg Gln Arg Thr Asn Ser Ile Gly His Asn Pro Pro
            660                 665                 670
His Trp Gly Ala Glu Arg Pro Phe Tyr Asn His Leu Gly Gly Asn Gln
            675                 680                 685
Val Ser Lys Glu Met Lys Arg Met Gly Phe Glu Asp Pro Lys Asp Lys
            690                 695                 700
Asn Ala Gln Glu Ser Ala Asn Pro Glu Asp Glu Val Asp Glu Phe Leu
705                 710                 715                 720
Gly Arg Ala Ile Asp Ala Arg Ser Ile Asp Arg Leu Arg Ser Glu His
                    725                 730                 735
Val Arg Lys Phe Leu Leu Thr Phe Arg Glu Pro Asp Leu Glu Lys Lys
            740                 745                 750
Tyr Ser Lys Gln Val Asp Asp Arg Phe Gly Ala Tyr Val Ala Cys Ala
            755                 760                 765
Ser Leu Val Phe Leu Phe Ile Cys Phe Val Gln Ile Thr Ile Val Pro
770                 775                 780
His Ser Ile Phe Met Leu Ser Phe Tyr Leu Thr Cys Ser Leu Leu Leu
785                 790                 795                 800
Thr Leu Val Val Phe Val Ser Val Ile Tyr Ser Cys Val Lys Leu Phe
                    805                 810                 815
Pro Ser Pro Leu Gln Thr Leu Ser Arg Lys Ile Val Arg Ser Lys Met
            820                 825                 830
Asn Ser Thr Leu Val Gly Val Phe Thr Ile Thr Leu Val Phe Leu Ala
            835                 840                 845
Ala Phe Val Asn Met Phe Thr Cys Asn Ser Arg Asp Leu Leu Gly Cys
850                 855                 860
Leu Ala Gln Glu His Asn Ile Ser Ala Ser Gln Val Asn Ala Cys His
865                 870                 875                 880
Val Ala Glu Ser Ala Val Asn Tyr Ser Leu Gly Asp Glu Gln Gly Phe
                    885                 890                 895
Cys Gly Ser Pro Trp Pro Asn Cys Asn Phe Pro Glu Tyr Phe Thr Tyr
            900                 905                 910
Ser Val Leu Leu Ser Leu Leu Ala Cys Ser Val Phe Leu Gln Ile Ser
            915                 920                 925
Cys Ile Gly Lys Leu Val Leu Met Leu Ala Ile Glu Leu Ile Tyr Val
            930                 935                 940
Leu Ile Val Glu Val Pro Gly Val Thr Leu Phe Asp Asn Ala Asp Leu
945                 950                 955                 960
Leu Val Thr Ala Asn Ala Ile Asp Phe Phe Asn Asn Gly Thr Ser Gln
                    965                 970                 975
Cys Pro Glu His Ala Thr Lys Val Ala Leu Lys Val Val Thr Pro Ile
            980                 985                 990
```

―continued

```
Ile Ile Ser Val Phe Val Leu Ala Leu Tyr Leu His Ala Gln Gln Val
        995             1000                1005

Glu Ser Thr Ala Arg Leu Asp Phe Leu Trp Lys Leu Gln Ala Thr Glu
   1010             1015                1020

Glu Lys Glu Glu Met Glu Glu Leu Gln Ala Tyr Asn Arg Arg Leu Leu
1025             1030                1035                1040

His Asn Ile Leu Pro Lys Asp Val Ala Ala His Phe Leu Ala Arg Glu
            1045                1050                1055

Arg Arg Asn Asp Glu Leu Tyr Tyr Gln Ser Cys Glu Cys Val Ala Val
            1060                1065                1070

Met Phe Ala Ser Ile Ala Asn Phe Ser Glu Phe Tyr Val Glu Leu Glu
        1075             1080                1085

Ala Asn Asn Glu Gly Val Glu Cys Leu Arg Leu Leu Asn Glu Ile Ile
        1090             1095                1100

Ala Asp Phe Asp Glu Ile Ile Ser Glu Asp Arg Phe Arg Gln Leu Glu
1105                1110                1115                1120

Lys Ile Lys Thr Ile Gly Ser Thr Tyr Met Ala Ala Ser Gly Leu Asn
                1125             1130                1135

Asp Ser Thr Tyr Asp Lys Val Gly Lys Thr His Ile Lys Ala Leu Ala
            1140                1145                1150

Asp Phe Ala Met Lys Leu Met Asp Gln Met Lys Tyr Ile Asn Glu His
        1155             1160                1165

Ser Phe Asn Asn Phe Gln Met Lys Ile Gly Leu Asn Ile Gly Pro Val
    1170                 1175                1180

Val Ala Gly Val Ile Gly Ala Arg Lys Pro Gln Tyr Asp Ile Trp Gly
1185                1190                1195                1200

Asn Thr Val Asn Val Ala Ser Arg Met Asp Ser Thr Gly Val Pro Asp
                1205                1210                1215

Arg Ile Gln Val Thr Thr Asp Met Tyr Gln Val Leu Ala Ala Asn Thr
            1220                1225                1230

Tyr Gln Leu Glu Cys Arg Gly Val Val Lys Val Lys Gly Lys Gly Glu
        1235                1240                1245

Met Met Thr Tyr Phe Leu Asn Gly Gly Pro Pro Leu Ser
1250                1255                1260
```